US006726938B2

(12) United States Patent
Han et al.

(10) Patent No.: US 6,726,938 B2
(45) Date of Patent: Apr. 27, 2004

(54) *FAGOPYRUM CYMOSUM* (TREV.) MEISN COMPOSITION, METHOD TO PREPARE AND ANALYZE THE SAME AND USES THEREOF

(76) Inventors: Pei Han, 100094 Yongfeng Road, Haidian District, Beijing (CN); Oiyu Guo, 100094 Yongfeng Road, Haidian District, Beijing (CN); Bo Chen, 100094 Yongfeng Road, Haidian District, Beijing (CN); Hongwu Zhu, 100094 Yongfeng Road, Haidian District, Beijing (CN)

( * ) Notice: Subject to any disclaimer, the term of this patent is extended or adjusted under 35 U.S.C. 154(b) by 52 days.

(21) Appl. No.: 09/785,953

(22) Filed: Feb. 16, 2001

(65) Prior Publication Data

US 2001/0018076 A1 Aug. 30, 2001

Related U.S. Application Data

(63) Continuation of application No. 09/161,251, filed on Sep. 26, 1998, now Pat. No. 6,451,353.

(30) Foreign Application Priority Data

Sep. 29, 1997 (CN) ........................................ 97116956 A

(51) Int. Cl.$^7$ ................................................ A61K 35/78
(52) U.S. Cl. ........................................ 424/725; 424/750
(58) Field of Search ................................ 424/725, 750

(56) References Cited

U.S. PATENT DOCUMENTS

| 4,673,530 A | 6/1987 | Hara |
| 4,906,656 A | 3/1990 | Laks et al. |
| 5,795,911 A | 8/1998 | Cheng et al. |
| 5,804,567 A | 9/1998 | Cheng et al. |
| 5,968,973 A | 10/1999 | Cheng et al. |

OTHER PUBLICATIONS

Ahmad N, et al. Suppression of nuclear transcription factor (NF [Kappa]B)—activation by green tea polyphenol (–) epigallocatechin–3–gallate. Proceedings of the American Association for Cancer Research. 1998;40:#3507. (Abstract in English).
Burns R, et al. Effect of arginine on the carcinogenicity of 7, 12–dimethylbenz [a]—anthracene and N–methyl–N–nitrosourea. Carcinogenesis Dec. 1984;5(12):1539–42. (Abstract from PubMed database, http://www.nim.nih.gov).
Chadwick D, et al. Bioactive compounds from plants. Ciba Foundation Symposium 154. New York 1990: John Wiley and Sons. A Wiley–Interscience Publication, ISBN 0–471–92691–4.
Chung L, et al. The influence of green tea epicatechin isomers on the growth of human cancer cells. Proceedings of the American Association for Cancer Research 1998;39:#2667. (Abstract in English).

De W. P, et al. Inhibition of epidermal growth factor receptor tyrosine kinase activity by hypericin. Biochem Pharmacol Dec. 3, 1993;46 (11):1929–36. (Abstract from PubMed database,http://www. nim.nih.gov).
Gao Y, et al. Reduced risk of esophageal cancer associated with green tea consumption. J Natl Cancer Inst Jun. 1, 1994;86(11):855–8. (Abstract from PubMed database, http://www.nim.nih.gov).
Gao Z, et al. Effect of Fagopyrum Cymosum Rootin on clonal formation of four human tumor cells. Chung Kuo Chung Yao Tsa Chih Aug., 1993; 18(8):498–500, 511. (Abstract from PubMed database, http://www.nim.nih.gov, Full article in Chinese).
Greenlee R, et al. Cancer Statistics, 2000. CA: A Cancer Journal For Clinicians 2000; 50:7–33. (http://ca–journal.org/articles/50/1/ 007–033/50–007–033.html).
Gupta S, et al. Involvement of nitric oxide during phthalocyanine (Pc4) photodynamic therapy–mediated apoptosis. Cancer Res May 1, 1998; 58(9):1785–8.
Han P, et al. Fagopyrum Cymosum (Trev.) Meisn Composition, Method to Prepare and Analyze the Same and Uses Thereof U.S. Ser. No. 09/161,251 filed on Sep. 26, 1998.
He J, et al. Oats and buckwheat intakes and cardiovascular disease risk factors in an ethnic minority of China. Am J Clin Nutr, 1995, 61:366–72.
Hollen P, et al. Quality of life assessment in individulas with lung cancer: testing the Lung Cancer Symptom Scale(LCSS). Eur J Cancer 1993; 29A Suppl 1: S51–8. (Abstract from PubMed database, http://www.nim.nih.gov).
Jassem J. Chemotherapy of advanced non–small cell lung cancer. Annals of Oncology 10 (Suppl.6):S77–S82, 1999; Kluwer Academic Publishers. Printed in the Netherlands.
Kayashita J, et al. Consumption of a buckwheat protein extract retards 7,12–dimethylbenz [alpha] anthracene–induced mammary carcinogenesis in rats. Biosci Biotechnol Biochem Oct. 1999; 63(10):1837–9.
Liang M, et al. Extracorporeal anticancer function of Fagopyrum Cymosum Rootin. Yannun Medicine 1991;12(6):364–9.
Ling X, et al. TLC Scanning Determination of Procyanidin B–2 in Fagopyrum Dibotrys's Roots and Stems. Chinese Journal of Pharmaceutical Analysis, 1990,10(4)pp. 227–230.

(List continued on next page.)

Primary Examiner—Jean C. Witz
(74) Attorney, Agent, or Firm—Albert Wai-Kit Chan; Mark Elkins

(57) ABSTRACT

This invention provides different compositions extracted from Fagopyrum cymosum (Trev.) Meisn. Said compositions comprise active components for therapeutic applications. This invention also provides a method of preparation of the compositions and a method of identification and determination of individual components of said compositions. Finally, this invention provides various uses of the compositions.

20 Claims, 1 Drawing Sheet

OTHER PUBLICATIONS

Liao J, et al. Growth inhibition, apoptosis inducation, and H202 production in human bronchial cancer cell lines by black tea theaflavins and green tea catachins. Proceedings of the American Association for Cancer Research 1998;40:#3513. (Abstract in English).

Liu T, et al. Change of active constituents in different development stages of Fagopyrum Cymosum Rhizome. Bulletin of Chinese Medicine, 1983, 8(6):5–6.

Liu w, et al. Some pharmacological properties of Jin Qiao Mai [Fagopyrum Cymosum (Trev.) Meisn]. Acta Pharmaceutica Sinica, 1981, 16(4):247–52.

Liu Y, et al. Studies on the chemical constituents of Fagopyrum Cymosum (Trev.)Meisn. Acta Pharmaceutica Sinica, 1983, 18(7):545–47.

Lu C, et al. Experiment of effects on blood–glucose and blood fat of fagopyrum Cymosum (Trev.) Meisn. Yunnan Chinese Medicine Research, 1980(3):45–46.

Lyn–Cook B, et al. Chemopreventive effects of tea extracts and various components on human pancreatic and prostate tumor cells in vitro. Nutr Cancer 1999;35(1):80–6. (Abstract from PubMed database, http://www.nim.nih.gov).

Ma M, et al. Mutagenicity and Teratogenicity tests of Fagopyrum Cymosum (Trev.) Meisn. Hereditas, 1991, 13(3):24–6.

Ma Y, et al. Prediction of responsiveness of human lung cancer xenografts to extracts of Fagopyrum Cymosim (Trev.) Meisn by SRC assay. Chinese Journal of Clinical Oncology 1989; 16(5):309–312.

Meng F, et al. Studies on anticancer effect of Jin E in vitro. Chinese Journal of Cancer 1996;13(3):265–6.

Meng F, et al. Anticancer Effect of Fagopyrum Cymosum Roots on Human Tumor Cells Cultured in vitro. Academic Journal of Kunming Medical College, 1994, 15(2):18–22.

Moumou Y, et al. Catechin production by callus caltures of Fagopyrum Esculentum. Phytochemistry, 1992, 31(4):1239–41.

Moumou Y, et al. Influence of culture conditions on polyphenol production by Fagopyrum Esculentum tissue cultures, Journal of Natural Products, 1992, 55(1):33–38.

Ohnishi O. Discovery of new Fagopyrum species and its implication for the studies of evolution of Fagopyrum and of the origin of cultivated buckwheat. The 6th International Symposium on Buckwheat. (http://soba.shinshu–u.ac.jp/contents/contents.html).

Peng Y, et al. Research and development of Fagopyrum Dibotrys. Chinese Herb, 1996, 27(10):629–31.

Samel D, et al. Selective inhibition of PK–C activity by Fagopyrum esculentum extract. Phytotherapy Research 1996;Vollo(Suppl.1):S156–S158.

Samel D, et al. The effect of purified extract of Fagopyrum Esculentum (Buckwheat)on protein kinases involved in signal transduction pathways. Planta Med Apr. 1996;62(2):106–10.

Trotin F, et al. Flavanol production by Fagopyrum Esculentum hairy and normal root cultures. Phytochemistry, 32(4):929–31.

Wang Z, et al. Inhibitory effect of green tea on the growth of established skin papillomas in mice. Cancer Res Dec. 1, 1992;52(23):6657–65 (Abstract from PubMed Database, http://www.nim.nih.gov).

Yao R, et al. Activity constituents of antitumor from Fagopyrum Cymosum. Acta Botanica Yunnanica 1989;11(2):215–8.

Zhang W, et al. Phenolic Constituents from Fagopyrum Dibotrys, Acta Botanica Yunnanica, 1994, 16(4):354–56.

Zhang Y, et al. Effects of Fagopyrum Cymosum (Trev.) Meisn for antibacterial and anti–infection. Yunnan Raise and Veterinarian, 1996 (2):5,22.

FAGOPYRUM CYMOSUM (TREV.) MEISN COMPOSITION, METHOD TO PREPARE AND ANALYZE THE SAME AND USES THEREOF

This application is a continuation application of U.S. Ser. No. 09/161,251, filed on Sep. 26, 1998, now U.S. Pat. No. 6,451,353, the content of which is incorporated my reference into this application.

Throughout this application, various publications are referenced and full citations for these publications may be found in the references at the end of the specifications preceding the claims. The disclosures of these publications are hereby incorporated by reference into this application in order to more fully describe the state of the art as known to the skilled therein as of the date of the invention described and claimed herein.

BACKGROUND OF THE INVENTION

*Fagopyrum cymosum* (Trev.) Meisn is a species of buckwheat, which belongs to the Genus Fagopyrum, family Polygonaceae. There are about 14 species of buckwheat, either cultivated or wild, existing around the world. Buckwheat grows mainly in the temperate area of Asia, Europe and North America. (1)

China was the earliest country in the world to cultivate buckwheat. According to archaeological studies, China began to grow buckwheat about 2,000 years ago. The genetic origins of buckwheat are believed to occur in Yunnan and Sichuan Provinces of China.(2) Buckwheat was brought from China to Japan via Korea Peninsula and then to Europe via Siberia and southern Russia. Germany was the first country in Europe to grow buckwheat in 1396. Then the crop was introduced into Belgium, France, Italy and Britain in the 17th century. Later buckwheat was brought to North America from the Netherlands.

At present, there are three best known species of buckwheat: common buckwheat (*Fagopyrum esculentum*), tartary buckwheat (*Fagopyrum tataricum*) and cymose buckwheat (*Fagopyrum cymosum*). The common buckwheat (*Fagopyrum esculentum*) is widely cultivated in the Northern Hemisphere. In China, it grows mainly in the northern and northwestern provinces. The tartary buckwheat (*Fagopyrum tataricum*) is cultivated primarily in the Himalayan area and south and southwest China. The cymose buckwheat (*Fagopyrum cymosum*) is basically a wild species, not available for human consumption as a crop, although some reports indicate that it is also cultivated in China on a small scale. The cymose buckwheat (*Fagopyrum cymosum*) distributes only in south and southwest China.

Although buckwheat is cultivated mainly as a minor crop around the world, it has been found recently that certain species of buckwheat also possess therapeutic properties. Animal tests and clinical trials in China have indicated that tartary buckwheat flour is effective in preventing and treating diabetes, hypertension, cerebral arteriosclerosis and cardiovascular disease. It also has the function of invigorating the stomach, facilitating digestion, enhancing the immune system and alleviating inflammation.(3)

The most important therapeutic property discovered in buckwheat is the anti-cancer effect of certain buckwheat species. For example, Samel, D. et al. reported in 1996 that they had examined the effect of a purified extract of the flowering herb of *Fagopyrum esculentum* on various protein kinases involved in signal transduction, finding that *Fagopyrum esculentum* contains red fluorescent compounds having photosensitizing properties. Spectrophotometric analysis of the extract indicated structural similarity to hypericin. Dose- and light-dependent inhibition of various protein kinases was observed. The purified *Fagopyrum esculentum* extract strongly inhibited two receptor-associated protein tyrosine kinases (EGF-R and Ins-R) and a Ser/Thr kinase (PK-C) at an ng/ml concentration range. Selectivity was exhibited as a decreased sensitivity to cytosolic PTKs and protein kinase CK-2. The protein kinases are important components of the signal transduction pathway. Aberration of signal transduction is a hallmark of several proliferative diseases. The researchers believed that the results of their experiment indicated that photosensitizing compounds in *Fagopyrum esculentum* are potential antiproliferative agents.(4)

In China, research on anti-cancer effect of buckwheat species was concentrated on *Fagopyrum cymosum* (Trev.) Meisn, which is also termed as *Fagopyrum dibotrys* (D. Don) Hara.

*Fagopyrum cymosum* (Trev.) Meisn has been used as a herbal medicine in China since ancient times, but mainly in combination with other medicinal herbs. Modern clinical studies conducted in China have shown that preparations of *Fagopyrum cymosum* (Trev.) Meisn can be used to treat lung abscess, bacillary dysentery and pyogenic infections. (5) Most importantly it has been found that preparations of *Fagopyrum cymosum* (Trev.) Meisn can be applied effectively for therapeutic purposes to various kinds of tumors.

Liu, W F et al. published an article in 1981 on some pharmacological properties of *Fagopyrum cymosum* (Trev.) Meisn, the root of which had been used for the treatment of pulmonary abscess. Liu pointed out that major active principle of *Fagopyrum cymosum* (Trev.) Meisn is flavanol (5, 7, 3', 4'-tetrahydroxyflan-3-01 dipolymers). Neither the extract of *Fagopyrum cymosum* (Trev.) Meisn nor flavanol exhibited significant antibacterial action in vitro. No antibacterial substance was found in the urine of either mice or human beings nor was it found in the organs of mice given the extract p. o. Liu indicated that therapeutic effect of *Fagopyrum cymosum* (Trev.) Meisn was shown in mice infected I. p. with *staphylococcus aureus* only when the extract of *Fagopyrum cymosum* (Trev.) Meisn or flavanol was given via the same route. Phagocytic action of peritoneal macrophages was enhanced, but the number of macrophages was not increased when the extract of *Fagopyrum cymosum* (Trev.) Meisn or flavanol was given I. p. to mice. Antipyretic action was demonstrated in rabbits. Flavanol was shown to be anti-inflammatory in mice and rats. Platelet aggregation in rats induced by ADP and *staphylococcus aureus* in vitro was inhibited by flavanol. The same effect on platelet aggregation induced by ADP and collagen was found when flavanol was given IV to rats. Flavanol given IV showed also expectorant effect in mice as shown by the phenol red method, but the bronchial excretion was not increased.(6)

Liu, Y L et al. in 1983 reported their research results on the chemical constituents of *Fagopyrum cymosum* (Trev.) Meisn. Liu indicated that they had isolated three components of *Fagopyrum cymosum* (Trev.) Meisn. Component A is the main constituent in *Fagopyrum cymosum* (Trev.) Meisn and accounts for its pronounced therapeutic effect on pulmonary abscess. The octamethylether, octamethylether diacetate and decanacetate derivatives were prepared from this component. On the basis of spectroscopic analyses, degradation products and physico-chemical constants, component A was identified as the dimer of 5, 7, 3', 4'-tetrahydroxyflavan-3-ol (C4–C8 linked), named dimeric procyanidin. Components B and C were identified as hecogenin and β-sitosterol respectively.(7)

Liu T C published an article in 1983 analyzing the growth and accumulation of active constituents during different development stages of *Fagopyrum cymosum* rhizome. The author reported that condensed procyanidin, the active constituent of *Fagopyrum cymosum* rhizome was observed and studied, including its existence in different parts of the plant and at different development stages, and its development in the root, stem and the above-the-ground part in different growth stages. The paper showed that the amount of condensed procyanidin is higher in the root and stem and is highest from mid-October till the withering season. The content rapidly increases from mid-June and reaches its highest level in late October.(8)

Yao R C et al. reported anti-tumor active constituents of cymose buckwheat in China in 1989. The researchers reported that they had extracted the active portion (A) from rhizome of cymose buckwheat using ethanol extraction, macroporous resin (D101) column chromatography and acetone extraction process. Chemical analysis revealed that A is a compound of proanthocyanidin, from which, in comparison with standard substances, (−) epicatechin, 3-galloyl (−) epicatechin, procyanidin B-2 and B-4, and 3,3'-digalloyl procyanidin B-2 had been detected. In the meantime, methylated, acetylated and trimethyl silica etherified derivatives of A had been prepared.(9)

Ma Y P et al. published an article in 1989 in China on prediction of responsiveness of human lung cancer xenograft to extracts of *Fagopyrum cymosum* (Trev.) Meisn by SRC assay. The researchers reported that they had determined responsiveness of human lung cancer explant to extracts E and CD1 of *Fagopyrum cymosum* (Trev.) Meisn by the method of subrenal capsule(SRC) assay. A total of 12 lung cancers had been tested in which 60 xenografts were implanted. With a mean growth of >5 OMU (1 OMU=0.02 mm) in the control animal an assay was considered evaluable. This study provided an evaluable assay rate of 83.3%. Taking <−10 OMU of tumor xenograft size as the standard of responsiveness extracts E and CD1 offered response rates of 40% and 20% respectively. Squamous cell carcinoma was more sensitive to E than other types of lung cancer. These findings were similar to the clinical effects of CD1 phase-I study. The study also confirmed that extracts E and CD1 had no toxicity or side effects in mice.(10)

Liang X Z et al. described using TLC scanning to determine procyanidin B-2 in *Fagopyrum dibotrys's* rhizome in an article published in China in 1990. The authors reported that procyanidin B-2 in *Fagopyrum cymosum* was determined by TLC scanning, taking high efficient silica gel 60F$^{254}$ as thin-layer absorbent, toluene-methylformaic-methanol-formic acid (1:2:0.2:0.1) as developing agent, Rf=0.21, scanned at 280 nm with CAMAG 76510 TLC scanner. The sample was prepared by leaching for 62 hours in methanol. The average recovery was 98%. Standard deviation was 0.0092, coefficient of variation is 1.8% (n=10).(11)

Liang, M D et al. published an article in 1991 on extra corporeal anti-cancer function of *Fagopyrum cymosum* rootin. The authors pointed out that *Fagopyrum cymosum* rootin (FCR) is a new anti-cancer medicine screening from *Fagopyrum cymosum* roots, with the method of extra corporeal culture of human cancer cell. The active constituent is large-moleculared condensed tannin D. At the concentration of 125 µg/ml, its inhibition ratio is 84.5% for SGC, 78.9% for Hela and 100% for KB, caused by the impairment of the cancer cell's membrane, RNA, DNA metabolization and cell nucleus cleavage.(12)

In the same year, Ma MF et al. reported the results of mutagenicitic and teratogenicitic tests of *Fagopyrum cymosum* (Trev.) Meisn. The results showed that no positive mutation was induced in four Ames standard bacterial strains (±S9), using seven different doses of *Fagopyrum cymosum* (Trev.) Meisn varying from 1–5,000 µg/plate. Antimutational effect was exhibited against reversional mutation of TA98 and TA 100 strains induced by daunorubicin and methyl methane sulphonate. No increase in micronucleus frequency in bone marrow polychromatophil erythroblast of NIH mice, no teratogenicity in Chinese hamster oocyte chromosomes (±S9), no adverse effect on reproductive capacity of NIH mice and development of mouse fetuses, nor teratogenicity of appearance, skeleton and internal organs of mouse fetuses were observed.(13)

Gao Z. et al. described in 1993 the effects of *Fagopyrum cymosum* root extract on proliferation of four human tumor cells in vitro in comparison with 5-FU. The researchers found that the proliferation of four human tumor cells were markedly inhibited by the extract and the inhibition rates were positively proportional to concentration. At the concentration of 12.5 micrograms/ml, the inhibition rates were 98.7% for GLC, 82.1% for KB, 65.4% for SGC and 53.8% for Hela cells.(14)

Zhang W J et al. discussed phenolic constituents from *Fagopyrum dibotrys* in 1994. The researchers reported that six phenolic constituents had been separated from the alcohol extracted powder of the dry rhizome of *Fagopyrum cymosum* (Trev.) Meisn. By polarimetry, HNMR, $^{13}$C-NMR and FAB-MS, they were identified as: 3,4-dihydroxybenzoic acid, gallic acid, (−) epicatechin, (−) epicatechin-3-O-gallate, procyanidin B-2 and procyanidin C-2.(15)

In the same year Meng F H et al. published an article on anticancer effect of cymose buckwheat roots on human tumor cells cultured in vitro. The researchers reported that anticancer effect of cymose buckwheat roots on various human cancer cells cultured in vitro had been studied using direct killing method, colony inhibition test and $^3$H-TdR incorporation test. The results showed that the drug at the concentration of 1 g·L$^{-1}$ had a killing rate of over one logasithmic killing against a number of human cancer cells, and when the concentration was lowered to 0.125 g·L$^{-1}$, its killing rate could still reach 74.3–92.1%, approximating one logasithmic killing. The extract from the roots of cymose buckwheat had significant anticancer effect, showing a colony inhibiting rate of 100% against several cancer cells when its concentration was 0.1 or 0.05 g·L$^{-1}$, and that of 75.1–89.2% at the concentration of 0.0125 g·L$^{-1}$. $^3$H-TdR labeling revealed that the drug could significantly inhibit nucleic acid metabolism in cancer cells, the inhibitory effect being close to that of positive control, fluorouracil, at the same concentration.(16)

In another article published in the same year, Meng F H et al. reported anticancer effect of Jin E in vitro. Jin E is a compound of tannin extracted from cymose buckwheat. In the studies on anticancer effect of Jin E, direct killing method, colony inhibition test and $^3$H-TdR radioautography were applied. Results of the studies showed that the 50% inhibiting concentrations of Jin E against GLC, Hela, SGC and KB cells were 67.8, 73.1, 79.9 and 83.0 µg/ml respectively, with a definite concentration and time-response relationship. Jin E at the concentrations of 100 and 50 µg/ml could completely inhibit colony formation of several human cancer cells, and Jin E at the concentration of 25 µg/ml had a colony inhibiting rate as high as 95% against four kinds of human cancer cells; the best anticancer activity was observed in Jin ED and alcohol soluble portion. Jin E at the high concentration (100 µg/ml) had an inhibiting rate of 87.9% against intracellular nucleic acid synthesis, the difference being very significant (P<0.01), compared with blank control group. It is concluded that Jin E has significant inhibitory effect on growth of multiple human cancer cells in vitro.(17)

Peng Yong et al. reported the research and development of *Fagopyrum dibotrys* in a paper published in China in 1996. The paper reviewed new developments in *Fagopyrum dibotrys* studies in the areas of the materia medica, the plant, the chemistry, the pharmacology, the clinic applications and the preparation of the medicine. The authors also provided suggestions on further exploitation and utilization of *Fagopyrum dibotrys*.(18)

SUMMARY OF THE INVENTION

Figure 1:
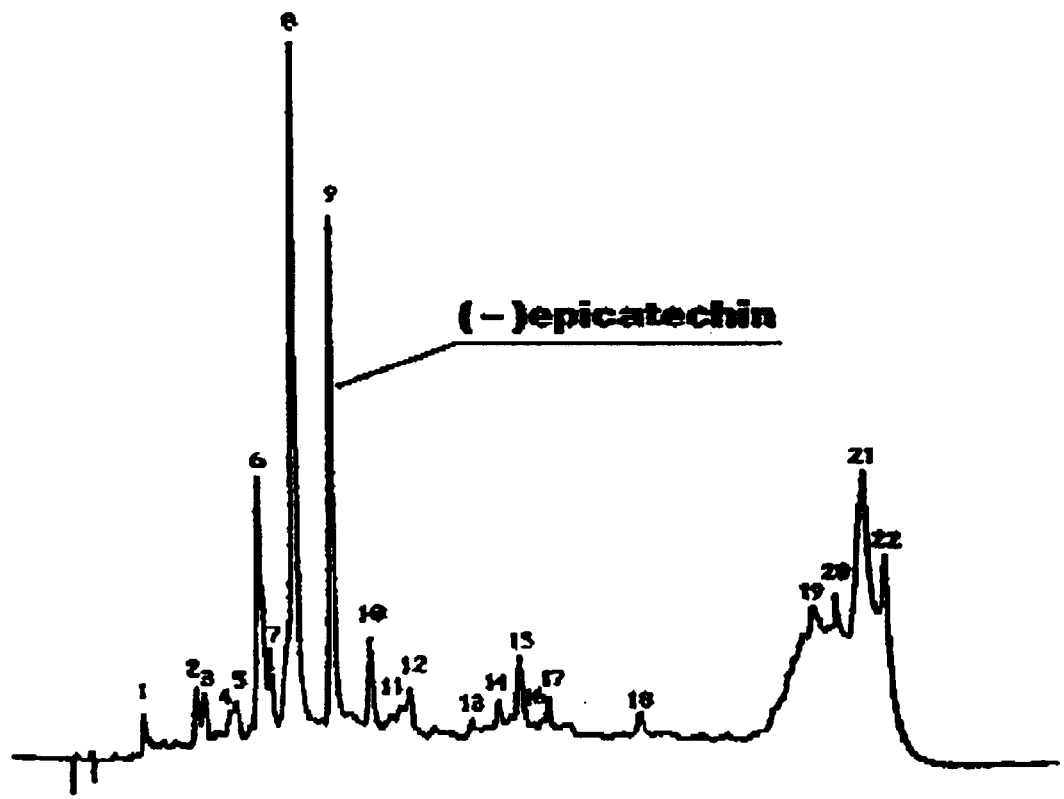
FIG. 1. HPLC profile of *Fagopyrum Ctmosum* (Trev.) Meisn

It is an object of the present invention to provide a *Fagopyrum cymosum* (Trev.) Meisn composition.

It is also an object of the present invention to provide a method of preparation of *Fagopyrum cymosum* (Trev.) Meisn compositions.

It is another object of the present invention to provide methods of identification and determination of individual active constituents of *Fagopyrum cymosum* (Trev.) Meisn compositions.

It is an additional object of the present invention to provide pharmaceuticals containing active constituents of *Fagopyrum cymosum* (Trev.) Meisn and apply the pharmaceuticals to treating lung cancer, gastric cancer, cervical cancer, sarcoma and other neoplasms, relieving inflammation, and alleviating toxic and adverse effects associated with chemotherapy and radiotherapy.

It is an additional object of the present invention to provide pharmaceuticals containing active constituents of *Fagopyrum cymosum* (Trev.) Meisn and apply the pharmaceuticals to treating coughing, caused by common cold, bronchitis, pneumonia, pulmonary tuberculosis, pulmonary abscess, lung cancer, and upper respiratory track infection.

The present invention relates generally to compositions extracted from *Fagopyrum cymosum* (Trev.) Meisn and particularly to *Fagopyrum cymosum* (Trev.) Meisn composition containing condensed tannins and procyanidins, including epicatechin, 3-O-galloyl-epicatechin, procyanidin B-2, B-4 and 3,3'-digalloyl-procyanidin B-2, etc. The invention is also concerned with methods of preparation of *Fagopyrum cymosum* (Trev.) Meisn compositions and methods of identification and determination of individual effective components of *Fagopyrum cymosum* (Trev.) Meisn compositions. In addition, the invention pertains to pharmaceuticals containing effective components of *Fagopyrum cymosum* (Trev.) Meisn and application of the pharmaceuticals. Accordingly, the present invention will be described in detail with respect to such fields of endeavor; however, those skilled in the art will appreciate that such description of the invention is meant to be exemplary only and should not be viewed as limitative of the full scope thereof.

DETAILED DESCRIPTION OF THE INVENTION

This invention provides a composition comprising 30–70% tannin content.

This invention provides a composition comprising 0.2–1.0% (–) epicatechin.

This invention provides a composition comprising 30–70% tannin content and 0.2–1.0% (–) epicatechin.

This invention provides a composition that when subjected to High Pressure Liquid Chromatography (HPLC) the 6 peak fingerprint shown in FIG. 1 and tabulated in Table 4 is produced. In this fingerprint the occurrence frequency (OF) of the 6 peaks are 80–100%; the retention time (RT) ratios of the 6 peaks in comparison with (–)epicatechin are 0.76, 0.88, 1.0, 1.12, 1.56, and 1.62 respectively; the area ratios of the 6 peaks in comparison with (–)epicatechin are 0.69, 1.80, 1.00, 0.20, 0.05 and 0.14 respectively; and the ranges of the area ratios of the 6 peaks in comparison with (–)epicatechin are 0.07–3.45, 0.18–9.0, 1.0, 0.02–3.0, 0.01–2.0 and 0.03–3.0 respectively.

This invention provides the above compositions having components extracted from *Fagopyrum cymosum* (Trev.) Meisn rhizome.

This invention provides the above compositions having components extracted from *Fagopyrum cymosum* (Trev.) Meisn rhizome that is obtained from cultivated plants.

This invention provides a method for obtaining a *Fagopyrum cymosum* (Trev.) Meisn composition comprising steps of: (1) obtaining, washing and cutting rhizome of fresh *Fagopyrum cymosum* (Trev.) Meisn; (2) drying the rhizome; (3) crushing the rhizome into particle; (4) putting the particle through a process of hot reflux in a solution selected from water, methanol, ethanol, acetone, water-methanol mixture, water-ethanol mixture, water-acetone mixture and ethyl acetate; (5) mixing the extracts; (6) separating the extract from precipitate and solid materials; (7) concentrating the separated extract; (8) diluting the extract with water; (9) passing the suspension through pretreated macro porous resin column; (10) eluting the chromatographic column; (11) concentrating the eluant at reduced pressure; (12) spray-drying the extract into amorphous red-brown powder, thereby producing an extract containing the active constituents of *Fagopyrum cymosum* (Trev.) Meisn.

This invention provides a method of extraction wherein the particle of *Fagopyrum cymosum* (Trev.) Meisn rhizome is put through a process of hot reflux. Comparing with other methods of extraction, such as maceration and percolation, the method of hot reflux consumes the smallest amount of time (less than 3 hours) and solvent, and provides highest yield and purity. By comparison, the method of maceration takes 7–10 days, consumes large quantity of solvent, and causes oxidation and polymerization of active constituents due to standing at the solvent state for a long time, that in turn decreases the therapeutic efficacy of the extract.

This invention provides a method of extraction wherein the solvent used in the process of hot reflux is ethanol.

This invention provides a method of extraction wherein the solvent used in the process of hot reflux is 10–90% ethanol.

Since various kinds of solvent can be used to extract the active constituents of *Fagopyrum cymosum* (Trev.) Meisn, researchers of this invention performed the following experiment to identify the solvent which produces the highest extraction yield. Considering the characteristics of the constituents of *Fagopyrum cymosum* (Trev.) Meisn and the strong polarity of the polyphenol mixtures, the researchers extracted 1 kg. particle of the rhizome of *Fagopyrum cymosum* (Trev.) Meisn respectively with four different solvents: ethanol, water, acetone and ethyl acetate. The extracts were dried by evaporation. Then the yields of the dried substances were calculated. The researchers found that the extract yield of ethanol was the highest and the others were ranked in the following order: water>acetone>ethyl acetate (Table 1).

TABLE 1

Extraction Yield of Different Solvent

| Solvent | Extraction Yield (%) |
|---|---|
| Ethanol | 8.88 |
| Water | 3.65 |
| Acetone | 1.65 |
| Ethyl acetate | 0.83 |

In another experiment, researchers of this invention found that the total tannin content in *Fagopyrum cymosum* (Trev.) Meisn extract by ethanol was significantly higher than that in the extract by acetone, indicating that purity of the former was higher than that of the latter. In the experiment, total tannin content in extracts by ethanol and acetone were determined by using a modified method for determination of tannin content, described in the appendix to the Pharmacopoeia of the People's Republic of China, 1995 edition. The results are shown in Table 2.

TABLE 2

Total Tanning Content in Extracts by Different Methods of Extraction

| Batch No. | Solvents | Total Tannin Content |
|---|---|---|
| 880206 | Ethanol | 73.47% |
| 880609 | Ethanol | 73.16% |
| 870513 | Ethanol | 71.97% |
| 870103 | Acetone | 67.16% |
| 880305 | Acetone | 59.93% |
| 880420 | Acetone | 58.97% |

In yet another experiment, researchers of this invention found that different solvents yield active constituents of *Fagopyrum cymosum* (Trev.) Meisn not only disparate in amount, but also different in cancer-inhibiting effects. The experiment showed that tumor-inhibiting rates of water and ethyl acetate extracts were lower than 30 percent and those of ethanol and acetone extracts were higher than 30 percent. The experiment also demonstrated that ethanol extract had higher anti-tumor efficacy than acetone extract (Table 3).

TABLE 3

Tumor-inhibiting Rates of *Fagopyrum cymosum* (Trev.) Meisn Extracted with Ethanol and Acetone

| Dosage* (mg/kg) | No. of Mice at Beginning/End | | Tumor-inhibiting Rate** (%) | |
|---|---|---|---|---|
| | Acetone Extract | Ethanol Extract | Acetone Extract | Ethanol Extract |
| 500 | 10/10 | 10/9 | 35.19 | 37.87 |
| 100 | 10/10 | 10/9 | 33.13 | 56.44 |
| 50 | 10/10 | 10/10 | 23.87 | 41.58 |
| 5-FU#10 | 10/10 | | 31.37 | |
| 0.5% CMC | 14/14 | | — | |

Note: *Mode of Administration × Times = p.o. × 10; **P < 0.01

All above experiments indicate that selection of an appropriate solvent is the key in the extraction of active constituents from *Fagopyrum cymosum* (Trev.) Meisn and that ethanol is the best solvent for this process. Ethanol extraction yields the highest amount of active constituents from the rhizome of *Fagopyrum cymosum* (Trev.) Meisn. It also demonstrates the best anti-cancer efficacy. In addition, ethanol is cheap, readily available, recoverable and preferred from the point of view of safety.

This invention provides a method of extraction wherein the particle of *Fagopyrum cymosum* (Trev.) Meisn rhizome is put through a process of hot reflux in the solvent of 10–90% ethanol with a ratio of 1:10 (W/V) twice (1–3 hours and 1–2 hours respectively) to produce extracts at the temperature of 50–70° C.

This invention provides a method of chromatography wherein the macroporous resins are packed in columns.

This invention provides a method of chromatography wherein the chromatographic material includes, but is not limited to porous polymer, silicon gel, aluminum oxide, polyamide, activated charcoal, cellulose or sephadex.

This invention provides a method of chromatography wherein the column is eluted with distilled water and 10–90% ethanol. The column is first eluted with distilled water in order to remove water soluble impurities, such as saccharides, pigments, organic acids and inorganic salts still present in the extracts while the active constituents are absorbed by macroporous resin. Then the column is eluted with 10–90% ethanol.

This invention provides a method of chromatography wherein color developing agent of phenol mixtures is ferric chloride reagent.

This invention provides a method of concentration wherein the chromatographic column eluant is concentrated at reduced pressure under 60° C. to a relative density of 1.10–1.13 since the tannin content of *Fagopyrum cymosum* (Trev.) Meisn is liable to change when heated.

This invention provides a method for obtaining a *Fagopyrum cymosum* (Trev.) Meisn composition comprising steps of: (1) obtaining, washing and cutting rhizome of fresh *Fagopyrum cymosum* (Trev.) Meisn; (2) drying the rhizome to containing less than 10% moisture; (3) crushing the rhizome into particle of the size smaller than 5 mm. in diameter while less than 10% of the particle of the size smaller than 0.1 mm. in diameter; (4) putting the particle through a process of hot reflux in the solution of 10–90% ethanol with a ratio of 1:10 (W/V) twice (1–3 hours and 1–2 hours respectively) to produce extracts at the temperature of 50–70° C.; (5) mixing the extracts; (6) separating the extract from precipitate and solid materials; (7) concentrating the separated extract at reduced pressure under the temperature of 70° C. at a density of 1.3 and a temperature of 50° C.; (8) diluting the extract with 5–10 times the amount of water; (9) passing the suspension through pretreated macroporous resin column (model D101 and other suitable polystyrene resin, saturated with water pre-column); (10) eluting the chromatographic column with distilled water and 80–90% ethanol repeatedly until the effluent does not react positively with ferric chloride reagent; (11) concentrating the eluant at reduced pressure under 50–70° C. to the density of 1.10–1.13; ethanol is completely recovered and the concentrate is free of alcohol; (12) spray-drying the extract into amorphous red-brown powder, thereby producing an extract containing the active constituents of *Fagopyrum cymosum* (Trev.) Meisn. The yield of powder totals 4–10% of the medicinal material. The total tannin content is 30–70% and the content of (−) epicatechin is 0.2–1.0%.

This invention provides a method of fingerprint chromatography for *Fagopyrum cymosum* (Trev.) Meisn composition comprising steps of: (1) preparing the assay comprising steps of: (a) dissolving 0.5 g. of *Fagopyrum cymosum* (Trev.) Meisn composition with 30 ml. of distilled water by ultrasonic treatment for 20 minutes; (b) removing the solution to the separator funnel; (c) extracting the solution from the water with chloroform (30 ml. each time for 3 times) in order to degrease; (d) continuously extracting the water layer with acetic ether (30 ml. each time for 5 times); (e) collecting and blending the acetic ether fractions; (f) drying the blend with anhydrous calcium chloride; (g) filter the blend; (h) drying the filtrate; (I) suspending the residue with water in constant volume of 10 ml.; (j) injecting 1 ml. of the suspension into $C_{18}$ods cartridge and eluting it with 5 ml. of water, 5 ml. of 50% methanol and 5 ml. of methanol respectively; (k) making the eluent of 50% methanol the constant volume of 5 ml. (l) filtering the eluent with 0.45 $\mu$ filtration membrane. (2) using (−) epicatechin as the standard; (3) performing HPLC assay under following conditions: (a) Gradient mobile phase:

| Time (minutes) | Water (PH = 3.00) | Acetonitrile |
|---|---|---|
| 0 | 90 | 10 |
| 40 | 74 | 26 |
| 50 | 20 | 80 |

(b) column temperature: room temperature; (c) flow rate: 0.8 ml/min; (d) injection volume: 10 $\mu$l; (e) wavelength: 282 nm; (f) calculating according to the following formula: (−) epicatechin=As×Cst/Ast×Ws×100% wherein As=peak area of sample, Cst=concentration of standard, Ast=peak area of standard, Ws=weight of sample.

This invention provides a method for determination of total tannin content in a *Fagopyrum cymosum* (Trev.) Meisn composition comprising steps of: (1) preparing the assay comprising steps of: (a) dissolving 3 g. of *Fagopyrum cymosum* (Trev.) Meisn composition with 20% ethanol in a 100 ml. volumetric flask; (b) diluting the solution to the mark; (c) separating the solution from the residue by filtration; (d) discarding the first filtrate; (e) drawing 75 ml. of subsequent filtrate; (f) evaporating the filtrate to the absence of ethanol on a water bath; (g) cooling the filtrate; (h) transferring the filtrate into a 250 ml. volumetric flask; (i) diluting the filtrate to the mark; (2) determining the total water soluble portion by evaporating 25 ml. of the assay to dryness and drying the precipitate at 105° C. for 3 hours ($T_1$); (3) determining the water soluble portion not bound with crude powder comprising steps of: (a) adding 6 g. of crude powder of *Fagopyrum cymosum* (Trev.) Meisn composition to 100 ml. of the assay and shaking for 15 minutes; (b) separating the solution from the residue by filtration; (c) evaporating 25 ml. of the filtrate to dryness; (d) drying the precipitate at 105° C. for 3 hours ($T_2$); (4) determining the water soluble portion of crude powder comprising steps of: (a) dissolving 6 g. of crude powder of *Fagopyrum cymosum* (Trev.) Meisn composition with 100 ml. of water; (b) shaking the solution for 15 minutes; (c) separating the solution from residue by filtration; (d) evaporating 25 ml. of the filtrate to dryness; (e) drying the precipitate at 105° C. for 3 hours ($T_0$). The total tannin content in percentage is calculated according to the following formula: Total tannin content %=$(T_1-T_2+T_0)\times10/W\times100\%$ wherein W=quantity of sample (dried substance).

This invention provides a method for determination of the amount of (−) epicatechin in a *Fagopyrum cymosum* (Trev.) Meisn composition comprising steps of: (1) performing adaptability test of the system under following conditions: (a) using octadecyl silicomethane-linked silica gel as the packing; (b) using water (pH 3.0)/acetonitrile for mobile phase gradient elution; the proportions being 0 minute: 90/10→40 minutes: 74/26→50 minutes: 20/80→110 minutes: stop; (c) making detection at the wavelength 282 nm; (d) the theoretical number of plate calculated with regard to (−) epicatechin should be no less than 20,000; (2) preparing the standard comprising steps of: (a) dissolving 10 mg. (−)epicatechin with 20 ml. of mobile phase solution by ultrasonic treatment in a 25 ml. volumetric flask (power not lower than 150 W, frequency not lower than 25 Hz) for 10 minutes; (b) removing the solution after complete dissolution; (c) cooling the solution to room temperature; (d) diluting the solution with mobile phase solution to the mark; (e) shaking the solution to homogeneity, 40 $\mu$g/ml (−)epicatechin is obtained; (3) preparing the assay comprising steps of: (a) dissolving 0.5 g. of the crude powder of *Fagopyrum cymosum* (Trev.) Meisn composition with 30 ml. of distilled water by ultrasonic treatment for 30 minutes; (b) transferring the solution to a separating funnel; (c) extracting and defatting the solution by chloroform for 3 times; (d) extracting the water layer with 30 ml. of ethyl acetate for 5 times; (e) pooling the ethyl acetate portions; (f) dehydrating the pooled ethyl acetate portions with anhydrous calcium chloride; (g) separating the residue by filtration; (h) volatilizing the filtrate to dryness; (i) making the precipitate into suspension with water with a constant volume of 10.0 ml.; (j) passing the assay from step (I) through $C_{18}$ ODS cartridge and performing solid phase extraction; (k) eluting the assay with 5 ml. of water, 50% methanol and methanol respectively, the 50% methanol portion having a constant volume of 5 ml.; (l) passing the 50% methanol portion through a filter membrane as the assay; (4) performing the assay comprising steps of: (a) pipetting the standard and the assay, 10 $\mu$l. each; (b) transferring the pipetted standard and assay into a liquid chromatograph; (c) performing the calculation and obtaining the results.

This invention provides a method wherein (−) epicatechin is used as the standard to identify (−) epicatechin in a *Fagopyrum cymosum* (Trev.) Meisn composition.

This invention provides a method wherein (−) epicatechin is used as the standard to determine the amount of (−) epicatechin in a *Fagopyrum cymosum* (Trev.) Meisn composition.

This invention provides a formulation containing the above compositions.

This invention provides the above formulation that can take the form of pill, capsule, granule, tablet, suspension, injection, syrup, tincture, or adhesive plaster.

This invention provides a pharmaceutical composition prepared according to the above methods, which comprises an effective amount of the above compositions and a pharmaceutically acceptable carrier.

For the purposes of this invention, "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion and various wetting agents. Other carriers may include additives used in tablets, coated tablets, granules and capsules, etc.

Typically such carriers contain excipients such as starch, milk, sugar, certain types of clay, gelatin, stearic acid or salts thereof, magnesium or calcium stearate, talc, vegetable fats or oils, gums, glycols or other known excipients. Such carriers may also include flavor and color additives or other ingredients. Compositions comprising such carriers are formulated by well known conventional methods.

This invention provides a pharmaceutical composition prepared according to the above methods, which comprises 1–99% of *Fagopyrum cymosum* (Trev.) Meisn compositions and 99–1% pharmaceutically acceptable carrier.

This invention provides a pharmaceutical composition prepared according to the above methods, which comprises 5–80% of *Fagopyrum cymosum* (Trev.) Meisn compositions and 95–20% pharmaceutically acceptable carrier.

This invention provides a pharmaceutical composition prepared according to the above methods, which comprises 10–75% of *Fagopyrum cymosum* (Trev.) Meisn compositions and 90–25% pharmaceutically acceptable carrier.

This invention provides a pharmaceutical composition prepared according to the above methods, which comprises 20–70% of *Fagopyrum cymosum* (Trev.) Meisn compositions and 80–30% pharmaceutically acceptable carrier.

This invention provides a pharmaceutical composition prepared according to the above methods, which comprises 65% of *Fagopyrum cymosum* (Trev.) Meisn compositions and 35% pharmaceutically acceptable carrier as the optimum ratio.

This invention provides a method for treating lung cancer in a subject by administering to the subject an effective amount of the above pharmaceutical compositions.

This invention provides a method for alleviating clinical symptoms in a subject suffering from lung cancer by administering to the subject an effective amount of the above pharmaceutical compositions.

This invention provides a method for alleviating the symptom of cough in a subject suffering from lung cancer by administering to the subject an effective amount of the above pharmaceutical compositions.

This invention provides a method for alleviating the symptom of expectoration in a subject suffering from lung cancer by administering to the subject an effective amount of the above pharmaceutical compositions.

This invention provides a method for alleviating the symptom of chest pain in a subject suffering from lung cancer by administering to the subject an effective amount of the above pharmaceutical compositions.

This invention provides a method for alleviating the symptom of bloody sputum in a subject suffering from lung cancer by administering to the subject an effective amount of the above pharmaceutical compositions.

This invention provides a method for alleviating the symptom of fever in a subject suffering from lung cancer by administering to the subject an effective amount of the above pharmaceutical compositions.

This invention provides a method for improving blood picture in a subject suffering from lung cancer by administering to the subject an effective amount of the above pharmaceutical compositions.

This invention provides a method for increasing hemoglobin count in a subject suffering from lung cancer by administering to the subject an effective amount of the above pharmaceutical compositions.

This invention provides a method for increasing leucocyte count in a subject suffering from lung cancer by administering to the subject an effective amount of the above pharmaceutical compositions.

This invention provides a method for increasing platelet count in a subject suffering from lung cancer by administering to the subject an effective amount of the above pharmaceutical compositions.

This invention provides a method for improving clinical signs in a subject suffering from lung cancer by administering to the subject an effective amount of the above pharmaceutical compositions.

This invention provides a method for increasing body weight in a subject suffering from lung cancer by administering to the subject an effective amount of the above pharmaceutical compositions.

This invention provides a method for increasing daily food consumption in a subject suffering from lung cancer by administering to the subject an effective amount of the above pharmaceutical compositions.

This invention provides a method for decreasing nausea occurrence in a subject suffering from lung cancer by administering to the subject an effective amount of the above pharmaceutical compositions.

This invention provides a method for decreasing vomiting occurrence in a subject suffering from lung cancer by administering to the subject an effective amount of the above pharmaceutical compositions.

This invention provides a method for decreasing diarrhea occurrence in a subject suffering from lung cancer by administering to the subject an effective amount of the above pharmaceutical compositions.

This invention provides a method for decreasing debility occurrence in a subject suffering from lung cancer by administering to the subject an effective amount of the above pharmaceutical compositions.

This invention provides a method for decreasing blood sedimentation rate in a subject suffering from lung cancer by administering to the subject an effective amount of the above pharmaceutical compositions.

This invention provides a method for decreasing blood urea nitrogen in a subject suffering from lung cancer by administering to the subject an effective amount of the above pharmaceutical compositions.

This invention provides a method for improving Karnofsky performance scores in a subject suffering from lung cancer by administering to the subject an effective amount of the above pharmaceutical compositions.

This invention provides a method for treating lung cancer in a subject by administering to the subject an effective amount of the above pharmaceutical compositions combined with chemotherapy.

This invention provides a method for treating lung cancer in a subject by administering to the subject an effective amount of the above pharmaceutical compositions combined with radiotherapy.

This invention provides a method for increasing Complement C3 level in a subject suffering from lung cancer by administering to the subject an effective amount of the above pharmaceutical compositions and combined with radiotherapy.

This invention provides a method for increasing E Rosette level in a subject suffering from lung cancer by administering to the subject an effective amount of the above pharmaceutical compositions combined with radiotherapy.

This invention provides a method for increasing lymphocyte transforming factor level in a subject suffering from lung cancer by administering to the subject an effective amount of the above pharmaceutical compositions combined with radiotherapy.

This invention provides a method for increasing IgA level in a subject suffering from lung cancer by administering to the subject an effective amount of the above pharmaceutical compositions combined with radiotherapy.

This invention provides a method for increasing IgG level in a subject suffering from lung cancer by administering to the subject an effective amount of the above pharmaceutical compositions combined with radiotherapy.

This invention provides a method for increasing IgM level in a subject suffering from lung cancer by administering to the subject an effective amount of the above pharmaceutical compositions combined with radiotherapy.

This invention provides a method for increasing macrophage phagocytic rate in a subject suffering from lung cancer by administering to the subject an effective amount of the above pharmaceutical compositions combined with radiotherapy.

This invention provides a method for increasing macrophage phagocytic index in a subject suffering from lung cancer by administering to the subject an effective amount of the above pharmaceutical compositions combined with radiotherapy.

This invention provides a method for treating gastric cancer, cervical cancer, sarcoma and other neoplasms, relieving inflammation, and alleviating toxic and adverse effects associated with chemotherapy and radiotherapy in a subject by administering to the subject an effective amount of the above pharmaceutical compositions.

This invention provides a method for treating coughing, caused by common cold, bronchitis, pneumonia, pulmonary tuberculosis, pulmonary abscess, lung cancer, and upper respiratory track infection.

The present invention is further explained by way of the following examples which are to be construed as merely illustrative and not limitative of the remainder of the disclosure in any way whatsoever.

Experimental Details

EXAMPLE 1

Preparation of *Fagopyrum cymosum* (Trev.) Meisn Pharmaceutical

1. Preparation of Raw Materials 370 kg. of *Fagopyrum cymosum* (Trev.) Meisn rhizome is obtained, washed, dried and crushed into 333 kg. of particle of the size less than 5 mm. in diameter, 20 kg. of that is of the size less than 0.1 mm in diameter.

2. Extraction

The above mentioned 333 kg. of particle is put into a stainless steel extractor. Then 1,000 kg. of 70% ethanol is added. Steam is introduced into the jacket of the extractor for heating to the constant temperature of 70° C. Stirring from the top is performed, the solid and liquid phases are fully mixed and the extraction is performed for 1.5 hours. The extract is drained out and filtered to remove fine particle impurities of the size larger than 0.05 mm. in diameter. The extract is kept in a stainless steel container.

Then 750 kg. of 70% ethanol is added, heated to the constant temperature of 70° C. and stirred. The extraction process is performed for 1 hour. The extract is drained out. The solid material is compressed, filtered, pooled and kept in a container. 1,600 kg. of extract is obtained.

3. Evaporation

The extract is continuously introduced into an evaporator, in which a vacuum degree of 500–600 mm Hg is maintained. The solvent is recovered. 170 kg. of condensed extract is obtained.

4. Separation through Macroporous Resin

The condensed extract is put into a suspension apparatus. 900 kg. of water is added. The suspension is maintained for 2 hours, filtered to remove fine particles of the size greater than 0.05 mm. in diameter, passed through AB-8 macroporous resin C for absorption and repeatedly washed with water. It is eluted with 700 kg. of 80% ethanol. 650 kg. of eluant is obtained. The solvent is recovered by vacuum evaporation. 130 g. of condensed eluant is obtained.

5. Drying

The condensed eluant is spray-dried. The temperature of influent air is controlled at 130–140° C., and that of effluent air at 65–70° C. The spray disc revolves at a speed of 8,000–10,000 rev/min. The spray keeps a speed of 300 kg/h. 17 kg. of red-brown amorphous powder is obtained. The powder comprises 63% of total tannin and 0.4% of (−) epicatechin.

6. Preparation of *Fagopyrum cymosum* (Trev.) Meisn Pharmaceutical 17 kg. of starch is fully mixed with the above mentioned red brown amorphous powder, then compressed into granules, with which #1 capsules are filled.

EXAMPLE 2

Preparation of *Fagopyrum cymosum* (Trev.) Meisn Pharmaceutical

1. Preparation of Raw Materials 280 kg. of *Fagopyrum cymosum* (Trev.) Meisn rhizome is obtained, washed, dried and crushed into 250 kg. of particle of the size less than 5 mm. in diameter, 18 kg. of that is of the size less than 0.1 mm in diameter.

2. Extraction

The above mentioned 250 kg. of particle is put into a $2m^3$ stainless steel extractor. Then 1000 kg. of 80% ethanol is added. Steam is introduced into the jacket of the extractor for heating to the constant temperature of 70° C. Stirring from the top is performed, the solid and liquid phases are fully mixed and the extraction is performed for 2 hours. The extract is drained out and filtered to remove fine particle impurities of the size larger than 0.05 mm. in diameter. The extract is kept in a stainless steel container.

Then 750 kg. of 80% ethanol is added, heated to the constant temperature of 70° C. and stirred. The extraction process is performed for 1.5 hour. The extract is drained out. The solid material is compressed, filtered, pooled and kept in a container. 1,550 kg. of extract is obtained.

3. Evaporation

The extract is continuously introduced into an evaporator, in which a vacuum degree of 500–600 mm Hg is maintained. The solvent is recovered. 170 kg. of condensed extract is obtained.

4. Separation through Macroporous Resin

The condensed extract is put into a suspension apparatus. 900 kg. of water is added. The suspension is maintained for 2 hours, filtered to remove fine particles of the size greater than 0.05 mm. in diameter, passed through AB-8 macroporous resin C for absorption and repeatedly washed with water. It is eluted with 700 kg. of 80% ethanol. 670 kg. of eluant is obtained. The solvent is recovered by vacuum evaporation. 130 kg. of condensed eluant is obtained.

5. Drying

The condensed eluant is spray-dried. The temperature of influent air is controlled at 130° C., and that of effluent air at 65° C. The spray disc revolves at a speed of 8,000 rev/min. The spray keeps a speed of 300 kg/h. 13.5 kg. of red-brown amorphous powder is obtained. The powder comprises 58.6% of total tannin and 0.98% of (−) epicatechin.

6. Preparation of *Fagopyrum cymosum* (Trev.) Meisn Pharmaceutical 13.5 kg. of starch is fully mixed with the above mentioned red brown amorphous powder, then compressed into granules, with which #1 capsules are filled.

EXAMPLE 3

Method of Fingerprint Chromatography for *Fagopyrum cymosum* (Trev.) Meisn Composition This invention provides a method of fingerprint chromatography for *Fagopyrum cymosum* (Trev.) Meisn composition comprising steps of: (1) preparing the assay comprising steps of: (a) ultrasonically dissolving 0.5 g. of *Fagopyrum cymosum* (Trev.) Meisn composition with 30 ml. of distilled water for 20 minutes; (b) removing the solution to the separator funnel; (c) extracting the solution from the water with chloroform (30 ml. each time for 3 times) in order to degrease; (d) continuously extracting the water layer with acetic ether (30 ml. each time for 5 times); (e) collecting and blending the acetic ether fractions; (f) drying the blend with anhydrous calcium chloride; (g) filtering the blend; (h) drying the filtrate; (i) suspending the residue with water in constant volume of 10 ml.; (j) injecting 1 ml. of the suspension into $C_{18}$ods cartridge and eluting it with 5 ml. of water, 5 ml. of 50% methanol and 5 ml. of methanol respectively; (k) making the eluent of 50% methanol the constant volume of 5 ml. (2) filtering the eluent with 0.45$\mu$ filtration membrane. (3) using (−) epicatechin as the standard; (4) performing HPLC assay under following conditions: (a) Gradient mobile phase:

| Time (minutes) | Water (PH = 3.00) | Acetonitrile |
| --- | --- | --- |
| 0 | 90 | 10 |
| 40 | 74 | 26 |
| 50 | 20 | 80 |

(b) column temperature: room temperature; (c) flow rate: 0.8 ml/min; (d) injection volume: 10 $\mu$l; (e) wavelength: 282 nm; (f) calculating according to the following formula: (−) epicatechin=As×Cst/Ast×Ws×100% wherein As=peak area of sample, Cst=concentration of standard, Ast=peak area of standard, Ws=weight of sample.

Fingerprint chromatography data and area ratio range are shown in Table 4.

TABLE 4

Fingerprint Chromatography Data and Area Ratio Range

| Peak # | Retention Time | Relative Retention Time | Appearance Probability | Area | Area Ratio | Area Ratio Range |
| --- | --- | --- | --- | --- | --- | --- |
| 6 | 14.57 | 0.76 | 80–100 | 705156 | 0.69 | 0.07–3.45 |
| 8 | 16.81 | 0.88 | 80–100 | 1833159 | 1.80 | 0.18–9.0 |
| 9 | 19.07 | 1.00 | 100 | 1018514 | 1.00 | |
| 10 | 21.45 | 1.12 | 80–100 | 208454 | 0.20 | 0.02–3.0 |
| 14 | 29.70 | 1.56 | 80–100 | 51306 | 0.05 | 0.01–2.0 |
| 15 | 30.91 | 1.62 | 80–100 | 145424 | 0.14 | 0.03–3.0 |

In an embodiment of the above method, (−) epicatechin is used as the standard to identify (−) epicatechin in a *Fagopyrum cymosum* (Trev.) Meisn composition.

EXAMPLE 4
Method for Determination of Total Tannin Content in a *Fagopyrum cymosum* (Trev.) Meisn Composition This invention provides a method for determination of total tannin content in a *Fagopyrum cymosum* (Trev.) Meisn composition comprising steps of: (1) preparing the assay comprising steps of: (a) dissolving 3 g. of *Fagopyrum cymosum* (Trev.) Meisn composition with 20% ethanol in a 100 ml. volumetric flask; (b) diluting the solution to the mark; (c) separating the solution from the residue by filtration; (d) discarding the first filtrate; (e) drawing 75 ml. of subsequent filtrate; (f) evaporating the filtrate to the absence of ethanol on a water bath; (g) cooling the filtrate; (h) transferring the filtrate into a 250 ml. volumetric flask; (i) diluting the filtrate to the mark; (2) determining the total water soluble portion by evaporating 25 ml. of the assay to dryness and drying the precipitate at 105° C. for 3 hours ($T_1$); (3) determining the water soluble portion not bound with crude powder comprising steps of: (a) adding 6 g. of crude powder of *Fagopyrum cymosum* (Trev.) Meisn composition to 100 ml. of the assay and shaking for 15 minutes; (b) separating the solution from the residue by filtration; (c) evaporating 25 ml. of the filtrate to dryness; (d) drying the precipitate at 105° C. for 3 hours ($T_2$); (4) determining the water soluble portion of crude powder comprising steps of: (a) dissolving 6 g. of crude powder of *Fagopyrum cymosum* (Trev.) Meisn composition with 100 ml. of water; (b) shaking the solution for 15 minutes; (c) separating the solution from residue by filtration; (d) evaporating 25 ml. of the filtrate to dryness; (e) drying the precipitate at 105° C. for 3 hours ($T_0$). The total tannin content in percentage is calculated according to the following formula: Total tannin content %=$(T_1-T_2+T_0)\times10/W\times100\%$ wherein W=quantity of sample (dried substance).

EXAMPLE 5
Method for Determination of the Amount of (−) Epicatechin in a *Fagopyrum cymosum* (Trev.) Meisn Composition This invention provides a method for determination of the amount of (−) epicatechin in a *Fagopyrum cymosum* (Trev.) Meisn composition comprising steps of: (1) performing adaptability test of the system under following conditions: (a) using octadecyl silicomethane-linked silica gel as the packing; (b) using water (pH 3.0)/acetonitrile for mobile phase gradient elution; (c) the proportions being 0 minutes: 90/10→40 minutes: 74/26→50 minutes: 20/80→110 minutes: stop; (d) making detection at the wavelength 282 nm; (e) the theoretical number of plate calculated with regard to (−)epicatechin should be no less than 20,000; (2) preparing the standard comprising steps of: (a) dissolving 10 mg. (−)epicatechin with 20 ml. of mobile phase solution by ultrasonic treatment in a 25 ml. volumetric flask (power not lower than 150 W, frequency not lower than 25 Hz) for 10 minutes; (b) removing the solution after complete dissolution; (c) cooling the solution to room temperature; (d) diluting the solution with mobile phase solution to the mark; (e) shaking the solution to homogeneity, 40 $\mu$g/ml (−) epicatechin is obtained; (3) preparing the assay comprising steps of: (a) dissolving 0.5 g. of the crude powder of *Fagopyrum cymosum* (Trev.) Meisn composition with 30 ml. of distilled water by ultrasonic treatment for 30 minutes; (b) transferring the solution to a separating funnel; (c) extracting and defatting the solution by chloroform for 3 times; (d) extracting the water layer with 30 ml. of ethyl acetate for 5 times; (e) pooling the ethyl acetate portions; (f) dehydrating the pooled ethyl acetate portions with anhydrous calcium chloride; (g) separating the residue by filtration; (h) volatilizing the filtrate to dryness; (i) making the precipitate into suspension with water with a constant volume of 10.0 ml.; (j) passing the assay from step (i) through $C_{18}$ ODS cartridge and performing solid phase extraction; (k) eluting the assay with 5 ml. of water, 50% methanol and methanol respectively, the 50% methanol portion having a constant volume of 5 ml.; (l) passing the 50% methanol portion through a filter membrane as the assay; (4) performing the assay comprising steps of: (a) pipetting the standard and the assay, 10 $\mu$l. each; (b) transferring the pipetted standard and assay into a liquid chromatograph; performing the calculation and obtaining the results.

In an embodiment of the above method, (−) epicatechin is used as the standard to determine the amount of (−) epicatechin in a *Fagopyrum cymosum* (Trev.) Meisn composition. The First Series of Experiments: Inhibiting Effect of the *Fagopyrum cymosum* (Trev.) Meisn Composition of this Invention on Mouse Sarcoma 180

Experimental Animals

Healthy Kunming and ICR mice with a body weight of 18–22 g. each were obtained from the breeding center of Sichuan Institute of Antibiotic Industry, Chengdu, Sichuan Province, P. R. China. Both male and female mice were used in the experiment.

Tumor Line

Sarcoma 180 was obtained from the Division of Pharmacology, Sichuan Institute of Antibiotic Industry, Chengdu, Sichuan Province, P. R. China.

Investigational Drug

The *Fagopyrum cymosum* (Trev.) Meisn composition of this invention was prepared into 0.5% CMC suspensions in concentrations needed. 5-Fluorouracil (5-FU) was purchased on the market and diluted to the concentration needed with saline.

Experimental Method

The experiment was carried out in vivo according to "Procedures of in vivo Screening of Antineoplastic Drugs" established in P. R. China in 1978.

Experimental Results

The inhibiting effect of the *Fagopyrum cymosum* (Trev.) Meisn composition of this invention on mouse sarcoma 180 is shown in Tables 5, 6, 7 and 8.

TABLE 5

Inhibiting Effect of the *Fagopyrum cymosum* (Trev.) Meisn composition of This Invention on ICR Mouse Sarcoma 180

| Dosage (mg/kg/d) | No. of Mice at beginning/end | Change in Mean Value of Body Weight (g) | Average Tumor Weight (g) ($\bar{x} \pm$ SD) | Tumor Inhibiting Rate (%) | P Value |
|---|---|---|---|---|---|
| 200 | 10/10 | +1.54 | 0.56 ± 0.21 | 44.55 | <0.001 |
| 100 | 10/10 | +1.86 | 0.44 ± 0.22 | 56.44 | <0.001 |
| 50 | 10/10 | +2.01 | 0.59 ± 0.17 | 41.58 | <0.001 |
| 0.5% CMC | 15/15 | +1.52 | 1.01 ± 0.25 | | |

Mode of administration × times = p.o. × 12

TABLE 6

Inhibiting Effect of the *Fagopyrum cymosum* (Trev.) Meisn Composition of This Invention on ICR Mouse Sarcoma 180

| Dosage (mg/kg/d) | No. of Mice at beginning/end | Change in Mean Value of Body Weight (g) | Average Tumor Weight (g) ($\bar{x} \pm$ SD) | Tumor Inhibiting Rate (%) | P Value |
|---|---|---|---|---|---|
| 10 | 10/9 | −0.90 | 0.60 ± 0.26 | 40.59 | <0.01 |
| 5 | 10/10 | +1.04 | 0.66 ± 0.84 | 34.65 | <0.05 |
| 5-Fu 5 | 10/10 | +2.01 | 0.49 ± 0.25 | 51.49 | <0.001 |

Mode of administration × times = i.p. × 12

TABLE 7

Inhibiting Effect of the *Fagopyrum cymosum* (Trev.) Meisn Composition of This Invention on Kunming Mouse Sarcoma 180

| Dosage (mg/kg/d) | No. of Mice at beginning/end | Change in Mean Value of Body Weight (g) | Average Tumor Weight (g) ($\bar{x} \pm$ SD) | Tumor Inhibiting Rate (%) | P Value |
|---|---|---|---|---|---|
| 500 | 10/9 | +1.98 | 1.96 ± 0.29 | 37.78 | <0.001 |
| 100 | 10/9 | +1.77 | 1.71 ± 1.07 | 45.71 | <0.01 |
| 20 | 10/8 | +3.65 | 2.11 ± 1.15 | 33.02 | <0.05 |
| 0.5% CMC | 21/20 | +4.67 | 3.15 ± 0.73 | | |

Mode of administration × times = p.o. × 10

TABLE 8

Inhibiting Effect of the *Fagopyrum cymosum* (Trev.) Meisn Composition of This Invention on Kunming Mouse Sarcoma 180

| Dosage (mg/kg/d) | No. of Mice at beginning/end | Change in Mean Value of Body Weight (g) | Average Tumor Weight (g) ($\bar{x} \pm$ SD) | Tumor Inhibiting Rate (%) | P Value |
|---|---|---|---|---|---|
| 40 | 10/8 | +0.45 | 1.63 ± 0.60 | 48.25 | <0.001 |
| 20 | 10/9 | +2.23 | 2.14 ± 0.55 | 32.06 | <0.001 |
| 10 | 10/8 | +3.05 | 2.15 ± 0.67 | 31.75 | <0.01 |
| 0.5% CMC | 21/20 | +4.67 | 3.15 ± 0.73 | | |

Mode of administration × times = i.p. × 12

Tables 5, 6, 7 and 8 show that the *Fagopyrum cymosum* (Trev.) Meisn composition of this invention by either oral or intraperitoneal administration is very effective in inhibiting the growth of mouse sarcoma 180.

The Second Series of Experiment: Inhibiting Effect of the *Fagopyrum cymosum* (Trev.) Meisn Composition of this Invention on Lewis Lung Carcinoma Experimental Animals Healthy C57BL/6N mice with a body weight of 18–22 g. each were obtained from the breeding center of Sichuan Institute of Antibiotic Industry, Chengdu, Sichuan Province, P. R. China. Both male and female mice were used in the experiment.

Tumor Line

Lewis lung carcinoma was obtained from the Division of Pharmacology, Sichuan Institute of Antibiotic Industry, Chengdu, Sichuan Province, P. R. China.

Investigational Drug

The *Fagopyrum cymosum* (Trev.) Meisn composition of this invention was prepared into 0.5% CMC suspensions in concentrations needed. 5-Fluorouracil (5-FU) was purchased on the market and diluted to the concentration needed with saline.

Experimental Method

The experiment was carried out in vivo according to "Procedures of in vivo Screening of Antineoplastic Drugs" established in P. R. China in 1978.

Experimental Results

The inhibiting effect of the *Fagopyrum cymosum* (Trev.) Meisn composition of this invention on Lewis lung carcinoma is shown in Tables 9, 10, 11 and 12.

TABLE 9

Inhibiting Effect of the *Fagopyrum cymosum* (Trev.)
Meisn Composition of This Invention on Lewis Lung Carcinoma

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 200* | 10/10 | +0.7 | 0.69 ± 0.37 | 55.48 | <0.05 |
| 100* | 10/10 | +1.3 | 0.91 ± 0.72 | 41.29 | <0.05 |
| 50* | 10/10 | +1.1 | 0.80 ± 0.51 | 48.39 | <0.05 |
| 5-Fu 5** | 9/9 | +0.4 | 0.74 ± 0.49 | 52.26 | <0.05 |
| 0.5% CMC* | 14/13 | +1.0 | 1.55 ± 1.07 | | |

*Mode of administration × times = p.o. × 10
**Mode of administration × times = i.p. × 10

TABLE 10

Inhibiting Effect of the *Fagopyrum cymosum* (Trev.)
Meisn Composition of This Invention on Lewis Lung Carcinoma

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 100 | 10/10 | −1.94 | 0.77 ± 0.24 | 41.22 | <0.01 |
| 50 | 10/10 | −1.74 | 0.86 ± 0.28 | 34.35 | <0.05 |
| 0.5% CMC | 10/10 | −1.31 | 1.31 ± 0.46 | | |

Mode of administration × times = p.o. × 10

TABLE 11

Inhibiting Effect of the *Fagopyrum cymosum* (Trev.)
Meisn Composition of This Invention on Lewis Lung Carcinoma

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 500 | 10/10 | −1.77 | 0.58 ± 0.38 | 25.64 | <0.05 |
| 100 | 10/10 | −0.52 | 0.41 ± 0.35 | 47.44 | <0.05 |
| 20 | 10/9 | −0.15 | 0.49 ± 0.30 | 37.18 | <0.05 |
| 0.5% CMC | 15/14 | −0.85 | 0.78 ± 0.42 | | |

Mode of administration × times = p.o. × 13

TABLE 12

Inhibiting Effect of the *Fagopyrum cymosum* (Trev.)
Meisn Composition of This Invention on Lewis Lung Carcinoma

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 40 | 10/7 | −1.35 | 1.33 ± 0.43 | 20.44 | <0.05 |
| 20 | 10/9 | −1.05 | 1.09 ± 0.43 | 34.79 | <0.05 |
| 10 | 10/9 | −0.75 | 1.57 ± 0.47 | 6.17 | <0.05 |
| 0.5% CMC | 14/14 | −0.67 | 1.67 ± 0.83 | | |

Mode of administration × times = i.p. × 10

Tables 9, 10, 11 and 12 show that the *Fagopyrum cymosum* (Trev.) Meisn composition of this invention is very effective in inhibiting the growth of Lewis lung carcinoma.

The Third Series of Experiment: Inhibiting Effect of the *Fagopyrum cymosum* (Trev.) Meisn Composition of this Invention on Mouse Cervical Carcinoma U14

Experimental Animals

Healthy Kunming and ICR mice with a body weight of 18–22 g. each were obtained from the breeding center of Sichuan Institute of Antibiotic Industry, Chengdu, Sichuan Province, P. R. China. Both male and female mice were used in the experiment.

Tumor Line

Uterine carcinoma U14 was obtained from the Division of Pharmacology, Sichuan Institute of Antibiotic Industry, Chengdu, Sichuan Province, P. R. China.

Investigational Drug

The *Fagopyrum cymosum* (Trev.) Meisn composition of this invention was prepared into 0.5% CMC suspensions in concentrations needed. 5-Fluorouracil (5-FU) was purchased on the market and diluted to the concentration needed with saline.

Experimental Method

The experiment was carried out in vivo according to "Procedures of in vivo Screening of Antineoplastic Drugs" established in P. R. China in 1978.

Experimental Results

The inhibiting effect of the *Fagopyrum cymosum* (Trev.) Meisn composition of this invention on mouse cervical carcinoma U14 is shown in Tables 13, 14, 15, 16 and 17.

TABLE 13

Inhibiting Effect of the *Fagopyrum cymosum* (Trev.)
Meisn Composition of This Invention on ICR Mouse Cervical Carcinoma U14

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 200* | 10/10 | +2.52 | 1.28 ± 0.38 | 35.03 | <0.001 |
| 100* | 10/10 | +2.16 | 1.14 ± 0.40 | 42.13 | <0.001 |
| 50* | 10/10 | +2.38 | 1.02 ± 0.29 | 48.22 | <0.001 |
| 5-Fu 5** | 10/10 | +3.93 | 1.27 ± 0.37 | 35.53 | <0.001 |
| 0.5% CMC* | 15/15 | +1.63 | 1.97 ± 0.45 | | |

*Mode of administration × times = p.o. × 10
**Mode of administration × times = i.p. × 9

TABLE 14

Inhibiting Effect of the *Fagopyrum cymosum* (Trev.)
Meisn Composition of This Invention on ICR Mouse Cervical Carcinoma U14

| Dosage (mg/kg/d) | No. of Mice at beginning/end | Change in Mean Value of Body Weight (g) | Average Tumor Weight (g) ($\bar{x} \pm SD$) | Tumor Inhibiting Rate (%) | P Value |
|---|---|---|---|---|---|
| 100 | 10/10 | −0.15 | 1.15 ± 0.21 | 26.28 | <0.01 |
| 50 | 10/9 | −0.18 | 1.01 ± 0.27 | 35.26 | <0.001 |
| 25 | 10/10 | −0.04 | 1.09 ± 0.21 | 30.13 | <0.001 |
| 0.5% CMC | 15/15 | −0.63 | 1.56 ± 0.40 | | |

Mode of administration × times = p.o. × 10

TABLE 15

Inhibiting Effect of the *Fagopyrum cymosum* (Trev.)
Meisn Composition of This Invention on Kunming Mouse
Mouse Cervical Carcinoma U14

| Dosage (mg/kg/d) | No. of Mice at beginning/end | Change in Mean Value of Body Weight (g) | Average Tumor Weight (g) ($\bar{x}$ ± SD) | Tumor Inhibiting Rate (%) | P Value |
|---|---|---|---|---|---|
| 500 | 11/11 | +4.26 | 3.74 ± 0.96 | 32.85 | <0.001 |
| 100 | 11/11 | +4.56 | 3.99 ± 1.16 | 28.37 | <0.01 |
| 0.5% CMC | 14/14 | +4.86 | 5.57 ± 1.31 | | |

Mode of administration × times = p.o. × 9

TABLE 16

Inhibiting Effect of the *Fagopyrum cymosum* (Trev.)
Meisn Composition of This Invention on Kunming
Mouse Cervical Carcinoma U14

| Dosage (mg/kg/d) | No. of Mice at beginning/end | Change in Mean Value of Body Weight (g) | Average Tumor Weight (g) ($\bar{x}$ ± SD) | Tumor Inhibiting Rate (%) | P Value |
|---|---|---|---|---|---|
| 40 | 10/8 | +1.81 | 3.39 ± 0.65 | 37.34 | <0.001 |
| 20 | 10/9 | +5.55 | 3.37 ± 0.66 | 29.05 | <0.01 |
| 10 | 10/9 | +3.90 | 4.08 ± 1.14 | 25.14 | <0.05 |
| 0.5% CMC | 10/10 | +5.25 | 5.45 ± 1.33 | | |

Mode of administration × times = i.p. × 10

TABLE 17

Inhibiting Effect of the *Fagopyrum cymosum* (Trev.)
Meisn Composition of This Invention on ICR Mouse
Cervical Carcinoma U14

| Dosage (mg/kg/d) | No. of Mice at beginning/end | Change in Mean Value of Body Weight (g) | Average Tumor Weight (g) ($\bar{x}$ ± SD) | Tumor Inhibiting Rate (%) | P Value |
|---|---|---|---|---|---|
| 10 | 10/8 | +0.57 | 1.56 ± 0.37 | 33.62 | <0.001 |
| 5 | 10/9 | +0.84 | 1.69 ± 0.40 | 28.09 | <0.01 |
| 5-Fu 5 | 10/10 | +1.25 | 1.55 ± 0.23 | 34.04 | <0.001 |
| 0.5% CMC | 10/13 | +0.03 | 2.35 ± 0.40 | | |

Mode of administration × times = i.p. × 10

Table 13, 14, 15, 16 and 17 show that the *Fagopyrum cymosum* (Trev.) Meisn composition of this invention is very effective in inhibiting the growth of mouse cervical carcinoma U14.

The Fourth Series of Experiment: Inhibiting Effect of the *Fagopyrum cymosum* (Trev.) Meisn Composition of this Invention on Colony Formation of Human Gastric Carcinoma Cell Line SGC-7901

Tumor Line

Human gastric cancer cell line SGC-7901 was obtained from Shanghai Institute of Materia Medica, Academia Sinica, Shanghai, P. R. China.

Cell Culture Vials

The round culture vials with a diameter of 40 mm. used in this experiment were procured from Jiangyin Glassworks, Jiangsu Province, P. R. China.

Investigational Drug

The *Fagopyrum cymosum* (Trev.) Meisn composition of this invention was weighed by aseptic technique and put into a sterile agate mortar. A few drops of dimethyl sulfoxide (DMSO) were added as complex solubilizer. It was finely ground and diluted with TC-199 culture medium to the concentrations needed.

Experimental Method

Cells were cultured in vitro according to the normal cell clone method. Eight experimental groups were established, with 3 vials for each group. The cells were exposed to the *Fagopyrum cymosum* (Trev.) Meisn composition of this invention for four time periods of 0.5, 4 and 8 hours, and 21 days. For the three sets of cells that were exposed to the drug for 0.5, 4 and 8 hours, the drug-containing culture medium was discarded. The cells were then washed with Hank's solution and added with 3 ml. fresh culture medium. The incubation of the fourth set of cells extended to day 21. The drug-containing culture medium was discarded. The cells were fixed with methyl alcohol and stained with Wright's and Giemsa stain. The number of colonies ($\geq$50 cells were taken as a colony) was counted. The colony forming efficiency (CFE) was calculated according to the equation "CFE=number of colony formation/total number of inoculated cells." Inhibition of colony formation (ICF) was calculated according to the equation "ICF%=(CFE of control group-CFE of exposed group)/CFE of control group× 100%."

Experimental Results

The inhibiting effect of the *Fagopyrum cymosum* (Trev.) Meisn composition of this invention on colony formation of Gastric Carcinoma Cell Line SGC-7901 is shown in Tables 18 and 19.

TABLE 18

Inhibiting Effect of the *Fagopyrum cymosum* (Trev.)
Meisn Composition of This Invention on Colony
Formation of SGC-7901 Cells (Colony Formation
Efficiency)

| Concentration ($\mu$g/ml) | 0.5 Hours | 4 Hours | 8 Hours | 21 Days |
|---|---|---|---|---|
| 0 | $8.5 \times 10^2$ | $10 \times 10^2$ | $7.7 \times 10^2$ | $10 \times 10^2$ |
| 0.48 | $8.2 \times 10^2$ | $9.7 \times 10^2$ | $5.9 \times 10^2$ | $7.4 \times 10^2$ |
| 1.92 | $7.6 \times 10^2$ | $8.7 \times 10^2$ | $5.0 \times 10^2$ | $6.6 \times 10^2$ |
| 7.8 | $6.9 \times 10^2$ | $8.4 \times 10^2$ | $4.4 \times 10^2$ | $5.1 \times 10^2$ |
| 31.3 | $4.9 \times 10^2$ | $5.4 \times 10^2$ | $2.5 \times 10^2$ | $2.8 \times 10^3$ |
| 125 | $3.9 \times 10^2$ | $4.5 \times 10^3$ | $1 \times 10^3$ | $6.7 \times 10^5$ |
| 500 | $2.6 \times 10^2$ | $2.3 \times 10^4$ | $4.4 \times 10^4$ | |
| 2000 | $9.7 \times 10^5$ | | | |

TABLE 19

Inhibiting Effect of the *Fagopyrum cymosum*
(Trev.) Meisn Composition of This Invention on Colony
Formation of SGC-7901 Cells (Inhibition of Colony
Formation)

| Concentration ($\mu$g/ml) | 0.5 Hours | 4 Hours | 8 Hours | 21 Days |
|---|---|---|---|---|
| 0 | | | | |
| 0.48 | 4 | 3 | 23 | 24 |
| 1.92 | 10 | 13 | 35 | 34 |
| 7.8 | 18 | 16 | 43 | 49 |
| 31.3 | 42 | 46 | 68 | 72 |
| 125 | 54 | 55 | 99 | 99.9 |
| 500 | 61 | 98 | 99.5 | 100 |
| 2000 | 99.9 | 100 | 100 | 100 |

Table 18 and 19 show that the *Fagopyrum cymosum* (Trev.) Meisn composition of this invention is very effective in inhibiting colony formation of human gastric carcinoma cell line SGC-7901.

The Fifth Series of Experiment: Alleviating Effect of the *Fagopyrum cymosum* (Trev.) Meisn Composition of this Invention on Xylene-induced Mouse Ear Inflammation Experimental Animals 49 healthy male adult Kunming mice were obtained from the breeding center of Sichuan Institute of Antibiotic Industry, Chengdu, Sichuan Province, P. R. China.

Investigational Drug

The *Fagopyrum cymosum* (Trev.) Meisn composition of this invention was prepared into 0.5% CMC suspensions in concentrations needed.

Experimental Method

Inflammation was induced in both ears of each mouse by local application of 0.05 ml. of xylene. The mice were then randomized into 3 groups. Half an hour later, one group received local application of 0.5% CMC suspension in right ear as the control. Two other groups were treated by the *Fagopyrum cymosum* (Trev.) Meisn composition of this invention in right ear in concentrations of 10 and 50 mg/ml respectively.

Mice were killed four hours after administration of the composition. Both left and right ears were excised. Holes 9 mm. in diameter were punched at the same part of both ears. The sections were weighed by a precision balance. The difference in weight between the two ears was used as indication of the intensity of inflammation.

Experimental Results

The alleviating effect of the *Fagopyrum cymosum* (Trev.) Meisn composition of this invention on xylene-induced mouse ear inflammation is shown in Table 20.

TABLE 20

Effect of the *Fagopyrum cymosum* (Trev.) Meisn Composition of This Invention in Alleviating Xylene-induced Mouse Ear Inflammation

| Concentration | No. of Mice | Average Weight of Inflamed Parts (mg $\bar{x} \pm$ SD) | P Value |
|---|---|---|---|
| 0.5% CMC | 17 | 6.94 ± 3.56 | |
| 10 mg/ml | 16 | 4.81 ± 3.90 | <0.05 |
| 50 mg/ml | 16 | 3.00 ± 2.31 | <0.001 |

Table 20 shows that the *Fagopyrum cymosum* (Trev.) Meisn composition of this invention is very effective in alleviating xylene-induced mouse ear inflammation.

The Sixth Series of Experiment: Radioprotective Effect of the *Fagopyrum cymosum* (Trev.) Meisn Composition of this Invention on Mice against $^{60}$Co Gamma-ray Whole Body Irradiation Experimental Animals 8–10 weeks old inbred balb/c and Kunming mice with a body weight of 22±2 g. each were obtained from the breeding center of Chengdu Institute of Biological Products, the Ministry of Health, Chengdu, Sichuan Province, P. R. China. Both male and female mice were used in the experiment.

Investigational Drug

The *Fagopyrum cymosum* (Trev.) Meisn composition of this invention of the batch number of 880208 was used in this experiment. The composition was finely ground in agate mortar, dissolved by dimethyl sulfoxide (DMSO) and diluted with saline to a concentration of 5–10 mg/ml (containing 2.5% DMSO).

Experimental Method

Mice were divided into 12 groups. The *Fagopyrum cymosum* (Trev.) Meisn composition of this invention was administered per os to mice at a dose of 0.2 ml. once a day. 2.5% DMSO in saline was administered to the control group. The drug schedule is shown in Tables 21, 22 and 23.

$^{60}$Co Radiation Source

Cobalt-60 therapy unit.

Irradiation Condition

Mice were fixed in special irradiation boxes, 5 mice per box. Then they were irradiated for 14 minutes at a distance of 75 cm. from the $^{60}$Co source to the center of the animals in an irradiation field of 20×20 cm. at a dose rate of 0.64–0.59 Gy/min. The whole body total irradiation dosage was 8 Gy.

Observation Parameters

After 8 GY of whole body irradiation, the number of dead mice in all groups was counted daily. The number of surviving mice in all groups was counted 30 days after irradiation. 30 day survival rates were calculated. The average surviving time of dead animals in all groups was also calculated.

Experimental Results

The radioprotective effect of the *Fagopyrum cymosum* (Trev.) Meisn composition of this invention on mice against $^{60}$Co gamma ray irradiation is shown by table 21, 22 and 23.

TABLE 21

Radioprotective Effect of the *Fagopyrum cymosum* (Trev.) Meisn Composition of This Invention on mice against Gamma Ray Irradiation (Balb/c Female Mice, Mode of Administration: p.o.)

| No of Mice | Dosage mg/ animal) | Schedule | 30 Day Survival Rate (%) | Increased Survival Rate (%) | Average Surviving Time of Dead Mice | Protection Efficacy | P Value |
|---|---|---|---|---|---|---|---|
| 20 | 0 | Once/day; 5, 4, 3, 2, 1 and 0 days before irradiation | 45 (9/20) | / | 17.9 | 1.00 | / |
| 20 | 0.5 | | 65 (13/20) | 20.0 | 10.0 | 0.98 | >0.05 |
| 19 | 1.0 | | 89.5 (17/19) | 44.5 | 12.0 | 1.21 | >0.01 |
| 21 | 2.0 | | 66.7 (14/21) | 21.7 | 15.1 | 1.16 | >0.05 |

TABLE 22

Radioprotective Effect of the *Fagopyrum cymosum* (Trev.) Meisn Composition of This Invention on Mice against Gamma Ray Irradiation (Kunming Male Mice, Mode of Administration: p.o.)

| No of Mice | Dosage mg/ Animal | Schedule | 30 Day Survival Rate (%) | Increased Survival Rate (%) | Average Surviving Time of Dead Mice | Protection Efficacy | P Value |
|---|---|---|---|---|---|---|---|
| 20 | 0 | Saline once/day; 6, 5, 4, 3, 2 and 1 days before irradiation | 5 (1/20) | / | 10.4 | 1.00 | / |

TABLE 22-continued

Radioprotective Effect of the *Fagopyrum cymosum*
(Trev.) Meisn Composition of This Invention on Mice against
Gamma Ray Irradiation (Kunming Male Mice, Mode of
Administration: p.o.)

| No of Mice | Dosage mg/ Animal | Schedule | 30 Day Survival Rate (%) | Increased Survival Rate (%) | Average Surviving Time of Dead Mice | Protection Efficacy | P Value |
|---|---|---|---|---|---|---|---|
| 10 | 1 | Once a day; 7, 6, 5, 4, 3, 2 and 1 days before irradiation | 20 (2/10) | 15 | 12.6 | 1.31 | >0.05 |
| 10 | 1 | Once a day; 3, 2 and 1 days before irradiation | 50 (5/10) | 45 | 10.5 | 1.65 | <0.005 |
| 20 | 1 | Once a day; 1 day before irradiation | 10 (2/20) | 5 | 12.6 | 1.03 | >0.05 |
| 20 | 1 | Once immediately before irradiation | 5 (1/20) | 0 | 12.1 | 0.99 | >0.05 |

TABLE 23

Radioprotective Effect of the *Fagopyrum cymosum*
(Trev.) Meisn Composition of This Invention on Mice against
Gamma Ray Irradiation (Kunming Female Mice, Mode of
Administration: po)

| No of Mice | Dosage mg/ animal | Schedule | 30 Day Survival Rate (%) | Increased Survival Rate (%) | Average Surviving Time of Dead Mice | Protection Efficacy | P Value |
|---|---|---|---|---|---|---|---|
| 20 | 0 | Saline once/day; 5, 4, 3, 2 and 1 days before irradiation | / | 13.5 | 13.5 | 1.00 | / |
| 20 | 1 | Once a day; 5, 4, 3, 2 and 1 days before irradiation | 45 (9/20) | 45 | 13 | 1.49 | <0.005 |
| 19 | 1 | Once a day; 3, 2 and 1 days before irradiation | 45 (9/20) | 42 | 13 | 1.53 | <0.005 |

Table 21, 22 and 23 show that the *Fagopyrum cymosum* (Trev.) Meisn composition of this invention is very effective in protecting mouse against $^{60}$Co gamma ray irradiation. The tables also show that gastric instillation of the *Fagopyrum cymosum* (Trev.) Meisn composition of this invention at different doses (0.5–2.0 mg/mouse) once a day 5, 4, 3, 2, 1 and 0 days before radiation exposure can protect mice against gamma ray irradiation to varying extent. Of all dose groups, the 1 mg. dose group shows the best effect with an increased survival rate of 44.5%. With the same dose of 1 mg, administration once a day, 3, 2 and 1 days before radiation exposure shows the best radio protective effect.

The Seventh Series of Experiment: Inhibiting Effect of the *Fagopyrum cymosum* (Trev.) Meisn Composition of this Invention in Combination with 5-Fluorouracil and $^{60}$Co Gamma Rays on Mouse Sarcoma 180

Experimental Animals

60 Kunming mice were obtained from the breeding center of Chengdu Institute of Biological Products, the Ministry of Health, Chengdu, Sichuan Province, P. R. China.

Tumor Line

Sarcoma 180 was obtained from the Division of Pharmacology, Sichuan Institute of Antibiotic Industry, Chengdu, Sichuan Province, P. R. China. The tumor line had been passed on several times in Kunming mice.

Investigational Drug

The *Fagopyrum cymosum* (Trev.) Meisn composition of this invention was used in the experiment.

5-Fluorouracil

The drug was prepared by Nantong Pharmaceuticals, Nantong, Jiangsu Province, P. R. China.

$^{60}$Co Radiation Source

Cobalt-60 therapy unit.

Experimental Method

Inoculation of tumor line and evaluation of therapeutic efficacy were performed according to "Procedures of in vivo Screening of Antineoplastic Drugs" established in P. R. China in 1978.

Sixty mice were divided into 6 groups, 10 mice for each group. Group 1 was the control group wherein the mice were treated only by saline. Groups 2 to 6 were treatment groups using different therapies. Group 2 was treated with the *Fagopyrum cymosum* (Trev.) Meisn composition of this invention. Group 3 was treated with 5-Fluorouracil. Group 4 was treated with $^{60}$Co irradiation. Group 5 was treated with the *Fagopyrum cymosum* (Trev.) Meisn composition of this invention combined with 5-Fluorouracil, while Group 6 was treated with the *Fagopyrum cymosum* (Trev.) Meisn composition of this invention combined with $^{60}$Co irradiation. Result of each group was then calculated and compared.

Experimental Results

The inhibiting effect of the *Fagopyrum cymosum* (Trev.) Meisn composition of this invention in combination with 5-fluorouracil and $^{60}$Co gamma ray irradiation on Mouse Sarcoma 180 is shown by Table 24.

TABLE 24

Inhibiting Effect of the *Fagopyrum cymosum* (Trev.) Meisn Composition of This Invention in Combination with 5-Fluorouracil and $^{60}$Co Gamma Ray Irradiation on Mouse Sarcoma 180

| Drug | Formulation | Dosage (mg/kg) | Mode of Administration and Schedule | No. of Mice at beginning /end | Tumor Weight (g) | Tumor Inhibiting Rate (%) |
|---|---|---|---|---|---|---|
| Saline | | 2.5% DMSO | p.o. × 10 | 10/10 | 1.36 | |
| Fagopyrum Composition | Powder | 100 | p.o. × 10 | 10/10 | 0.88 | 35.2 |
| 5-FU | Injection | 5 | i.p. × 10 | 10/10 | 0.71 | 47.8 |
| γ-Irradiation | | 300 rad | 3 days after inoculation | 10/10 | 0.57 | 50.7 |
| Fagopyrum Composition + 5-FU | Powder + Injection | 100 mg + 5 mg | p.o. × 10 i.p. × 10 | 10/9 | 0.62 | 54.4 |
| Fagopyrum Composition + γ-Irradiation | Powder | 100 mg + 300 rad | p.o. × 10 300 rad × 1 | 10/9 | 0.44 | 67.6 |

Table 24 shows that the *Fagopyrum cymosum* (Trev.) Meisn composition of this invention when applied in combination with 5-Fluorouracil and $^{60}$Co gamma ray irradiation is more effective than other experimental therapies in inhibiting the growth of Mouse Sarcoma 180.

The First Series of Clinical Study: Anticancer Effect of the Pharmaceutical Composition of *Fagopyrum cymosum* (Trev.) Meisn of this Invention Patient Selection 136 patients with lung cancer were recruited in the clinical study. Their age and sex distributions were as follows:

TABLE 25

Age and Sex Distribution of 136 Lung Cancer Patients

| | Total Cases | | Age | |
|---|---|---|---|---|
| Sex | Cases | % | Range of Age | Mean Value of Age |
| Male | 102 | 75% | 34–75 | 61 |
| Female | 34 | 25% | 31–80 | 60 |

The major clinical symptoms of the 136 patients were as follows:

TABLE 26

Major Clinical Symptoms of 136 Lung Cancer Patients

| | Total | Cough | Expectoration | Chest Pain | Bloody Sputum | Fever |
|---|---|---|---|---|---|---|
| Cases | 136 | 122 | 118 | 82 | 57 | 37 |
| % | 100 | 89.7 | 86.8 | 60.3 | 41.9 | 27.2 |

The radiographic presentations of the 136 patients were as follows:

TABLE 27

Radiographic Presentations of 136 Lung Cancer Patients

| | Total | Centrally Located Lesions | Peripheral Lesion |
|---|---|---|---|
| Cases | 136 | 118 | 18 |
| % | 100 | 86.78 | 13.22 |

The 136 patients were staged based on "The Guiding Principles for Clinical Research of New Drugs (Traditional Chinese Materia Medica)" established by the Ministry of Health of P. R. China in 1988. Table 28 shows that the majority of the 136 patients fell into intermediate and late stages of lung cancer.

TABLE 28

Clinical Stages of 136 Lung Cancer Patients

| | Total | I | II | III | IV | III + IV |
|---|---|---|---|---|---|---|
| Cases | 136 | 6 | 37 | 61 | 32 | 93 |
| % | 100 | 4.41 | 27.21 | 44.85 | 23.53 | 68.38 |

The pathological classifications of the 136 patients were as follows:

TABLE 29

Pathological Classifications of 136 Lung Cancer Patients

|  | Total | Squamous Cell Carcinoma | Adeno-carcinoma | Small Cell Undifferentiated Carcinoma | Large Cell Carcinoma | Unclassified |
|---|---|---|---|---|---|---|
| Cases | 136 | 77 | 44 | 12 | 1 | 2 |
| % | 100% | 56.62% | 32.35% | 8.82% | 0.74% | 1.47% |

Methods of Diagnosis: All enrolled patients were diagnosed by detection of lung cancer cells through biopsy or brushing in fiberopic bronchoscopy, pathological biopsy of lymph nodes, biopsy by needle aspiration or pathological examination of sputum or pleural effusion.

Design of the Clinical Study

All patients were administered orally the pharmaceutical composition of *Fagopyrum cymosum* (Trev.) Meisn of this invention in the formulation of capsule (containing 200 mg. of the active components), 1.2–1.6 g. each time, 3 times a day. Patients took the medicine only after meals. The duration of treatment was 2 months.

No patient received anticancer chemotherapy or radiotherapy prior to or during the course of the clinical study.

Evaluation of Therapeutic Effectiveness

Therapeutic effectiveness of the pharmaceutical composition of *Fagopyrum cymosum* (Trev.) Meisn of this invention was evaluated according to the established criteria of four grades: Complete Remission (CR), Partial Remission (PR), Stableness (S) and Progression (P).

Therapeutic Results

The results of clinical study show that the pharmaceutical composition of *Fagopyrum cymosum* (Trev.) Meisn of this invention is effective in treating lung cancer.

1. The pharmaceutical composition of *Fagopyrum cymosum* (Trev.) Meisn of this invention is effective in treating lung cancer.

TABLE 30

Effects of the Pharmaceutical Composition of *Fagopyrum cymosum* (Trev.) Meisn of This Invention in Treating Lung Cancer Patients

|  | Total | CR | PR | S | P | CR + PR |
|---|---|---|---|---|---|---|
| Cases | 136 | 1 | 17 | 79 | 39 | 18 |
| % | 100 | 0.74 | 12.5 | 58.08 | 28.68 | 13.24 |

2. The pharmaceutical composition of *Fagopyrum cymosum* (Trev.) Meisn of this invention is effective in alleviating major clinical symptoms of lung cancer.

TABLE 31

Effects of the Pharmaceutical Composition of *Fagopyrum cymosum* (Trev.) Meisn of This Invention in Alleviating Major Clinical Symptoms of Lung Cancer Patients

|  |  | No. of Cases | | Change | |
|---|---|---|---|---|---|
|  |  | Before | After | | |
| Symptom | Severity | Treatment | Treatment | Number | % |
| Cough | Mild | 62 | 79 | +17 | +27.4% |
|  | Moderate | 46 | 18 | −28 | −60.9% |
|  | serious | 14 | 7 | −7 | −50% |
|  | Total | 122 | 104 | −18 | −14.8% |

TABLE 31-continued

Effects of the Pharmaceutical Composition of *Fagopyrum cymosum* (Trev.) Meisn of This Invention in Alleviating Major Clinical Symptoms of Lung Cancer Patients

|  |  | No. of Cases | | Change | |
|---|---|---|---|---|---|
|  |  | Before | After | | |
| Symptom | Severity | Treatment | Treatment | Number | % |
| Expectoration | Mild | 80 | 60 | −20 | −25% |
|  | Moderate | 35 | 16 | −19 | −54.3% |
|  | serious | 3 | 1 | −2 | −66.7% |
|  | Total | 118 | 77 | 41 | −34.7% |
| Chest Pain | Mild | 57 | 46 | −11 | −19.3% |
|  | Moderate | 19 | 8 | −11 | −57.9% |
|  | serious | 6 | 3 | −3 | −50% |
|  | Total | 82 | 57 | −25 | −30.5% |
| Bloody Sputum | Mild | 47 | 24 | −23 | −48.9% |
|  | Moderate | 9 | 4 | −5 | −55.6% |
|  | serious | 1 | 0 | −1 | −100% |
|  | Total | 57 | 28 | −29 | −50.9% |
| Fever | Mild | 29 | 13 | −16 | −55.2% |
|  | Moderate | 8 | 2 | −6 | −75% |
|  | serious | 1 | 2 | +1 | +100% |
|  | Total | 38 | 17 | −21 | −55.3% |

$p < 0.05$

Expectoration: Mild < 50 ml/day, Moderate < 100 ml/day, serious > 100 ml/day

3. The pharmaceutical composition of *Fagopyrum cymosum* (Trev.) Meisn of this invention is effective in improving blood picture of lung cancer patients by increasing their hemoglobin, leucocyte and platelet counts.

TABLE 32

Effects of the Pharmaceutical Composition of *Fagopyrum cymosum* (Trev.) Meisn of This Invention in Improving Blood Picture of Lung Cancer Patients

| Blood Count | Total | | Increased | | Stable | | Decreased | | $X^2$ |
|---|---|---|---|---|---|---|---|---|---|
|  | No. | % | No. | % | No. | % | No. | % | |
| Hemoglobin | 136 | 100 | 68 | 50 | 25 | 18.4 | 43 | 31.6 | 6.42 |
| Leucocyte | 136 | 100 | 14 | 10.3 | 120 | 88.2 | 2 | 1.5 | 8 |
| Platelet | 136 | 100 | 6 | 4.4 | 129 | 94.9 | 1 | 0.7 | 3.69 |

Increase or decrease of hemoglobin count denotes exceeding 0.5% above or below normal value, while those for leucocyte and platelet counts denote the values above or below normal range; $p < 0.05$.

4. The pharmaceutical composition of *Fagopyrum cymosum* (Trev.) Meisn of this invention is effective in improving clinical signs of lung cancer patients.

After treatment by the pharmaceutical composition of *Fagopyrum cymosum* (Trev.) Meisn of this invention, the 136 lung cancer patients generally gained weight and better appetite, decreased blood sedimentation rate and improved kidney function. There was no significant change of liver function after the treatment.

TABLE 33

Effects of the Pharmaceutical Composition of *Fagopyrum cymosum* (Trev.) Meisn of This Invention in Improving Clinical Signs of Lung Cancer Patients.

| Clinical Signs | Before Treatment | After Treatment |
|---|---|---|
| Average Weight (kg.) | 57.2 | 57.5 |
| Average Daily Food Consumption (g.) | 588 | 660 |

TABLE 33-continued

Effects of the Pharmaceutical Composition of
Fagopyrum cymosum (Trev.) Meisn of This Invention in
Improving Clinical Signs of Lung Cancer Patients.

| Clinical Signs | Before Treatment | After Treatment |
|---|---|---|
| Average Blood Sedimentation Rate (mm/h) | 24.8 | 23.5 |
| Average Blood Urea Nitrogen (mmol/L) | 4.76 | 3.97 |

During the clinical study, the pharmaceutical composition of *Fagopyrum cymosum* (Trev.) Meisn of this invention brought out a combined complete and partial remission rate of 13.24% and a stable rate of 58.08%. It alleviated to a varying degree various clinical symptoms of lung cancer, such as cough, expectoration, chest pain, bloody sputum and fever. The pharmaceutical composition of *Fagopyrum cymosum* (Trev.) Meisn of this invention also improved blood picture of lung cancer patients by increasing their hemoglobin, leucocyte and platelet counts. In addition, it improved various clinical signs of lung cancer patients. Of 136 patients, one achieved complete remission. These results indicate that the pharmaceutical composition of *Fagopyrum cymosum* (Trev.) Meisn of this invention is effective in treating lung cancer.

The Second Series of Clinical Study: Alleviating Effect of the Pharmaceutical Composition of *Fagopyrum cymosum* (Trev.) Meisn of this Invention on the Toxicity and Other Side-effects of Anticancer Chemotherapeutic Agents Patient Selection 60 patients with lung cancer were recruited in the clinical study. 35 patients were male and 25 patients were female. They aere 35–76 years old with an average age of 55.5. Their age distribution is as follows (Table 34):

TABLE 34

Age Distribution of 60 Lung Cancer Patients

| | Total | <40 | 40–60 | 61–70 | >70 |
|---|---|---|---|---|---|
| number | 60 | 6 | 24 | 22 | 8 |
| % | 100 | 10 | 40 | 36.67 | 13.33 |

All patients were hospitalized with definite diagnosis of lung cancer confirmed pathologically. Their clinical stages are shown in Table 35.

TABLE 35

Clinical Stages of 60 Lung Cancer Patients

| | Total | I | II | III | IV | III ± IV |
|---|---|---|---|---|---|---|
| Cases | 60 | 0 | 6 | 28 | 26 | 54 |
| % | 100 | 0 | 10 | 46.7 | 43.3 | 90 |

Table 35 shows that patients in stage III and IV accounted for 90% of the total. The pathological classifications of the patients are as follows:

TABLE 36

Pathological Classifications of 60 Lung Cancer Patients

| | Total | Squamous Cell Carcinoma | Adeno-carcinoma | Small Cell Carcinoma |
|---|---|---|---|---|
| Cases | 60 | 16 | 40 | 4 |
| % | 100 | 26.67 | 66.67 | 6.66 |

48 patients (80%) had received radiotherapy or chemotherapy six or three months before they were enrolled in the clinical study.

Design of the Clinical Study

The 60 lung cancer patients were randomly divided into a treatment group and a control group, 30 patients in each group. Patients in the treatment group were administered orally of the pharmaceutical composition of *Fagopyrum cymosum* (Trev.) Meisn of this invention at the dose of 1.6 g. (8 capsules), three times a day. They might take symptomatic drugs at the same time, but no other anticancer drugs. The control group was treated by chemotherapy, mainly with cisplatium, VP-16 and CAP program. Patients with squamous carcinoma were further treated with daunorubicin and intrapleural therapy mainly by MMC and DDP programs. Patients with small cell carcinoma were further treated mainly with CEA program while patients with non-small cell carcinoma were further treated with CAP program.

Before the treatment started, patients in both groups took cardiac, renal, hepatic, bone marrow and immune function examinations at the same time. Two months after medication, they were examined again for the same parameters of various functions.

Evaluation of Therapeutic Effectiveness

Therapeutic effectiveness of the Pharmaceutical composition of *Fagopyrum cymosum* (Trev.) Meisn of this invention was evaluated according to the established criteria of four grades: Complete Remission (CR), Partial Remission (PR), Stableness (S) and Progression (P). Toxic reaction was evaluated according to the unified criteria for grading acute, subacute and toxic reactions of anticancer drugs. They are divided into grade 0, I, II, III and IV.

Therapeutic Results

1. The pharmaceutical composition of *Fagopyrum cymosum* (Trev.) Meisn of this invention is effective in treating lung cancer.

Two months after medication, no complete remission was observed. The partial remission rate in the control group was higher than that in the treatment group. The stableness rate in the treatment group was significantly higher than that in the control group. The combined rate of PR+S in the treatment group (83.33%) was higher than that in the control group (63.33%). The number of patients with progression of tumor in the control group were about 2 times more than that in the treatment group. The data indicate that the pharmaceutical composition of *Fagopyrum cymosum* (Trev.) Meisn of this invention is effective in treating lung cancer.

TABLE 37

Effects of the Pharmaceutical Composition of
Fagopyrum cymosum (Trev.) Meisn of This Invention in
Treating Lung Cancer

| Group | Total | CR (%) | PR (%) | S (%) | P (%) | PR + S (%) |
|---|---|---|---|---|---|---|
| Treatment | 30 | 0 (0) | 6 (20.00) | 19 (63.33) | 5 (16.67) | 25 (83.33) |
| Control | 30 | 0 (0) | 8 (26.66) | 11 (36.67) | 11 (36.67) | 19 (63.33) |

2. The pharmaceutical composition of *Fagopyrum cymosum* (Trev.) Meisn of this invention achieves its therapeutic effect with less toxic reaction than chemotherapy.

TABLE 38

Comparison of Toxic Reactions between the Treatment Group Receiving the Pharmaceutical Composition of *Fagopyrum cymosum* (Trev.) Meisn of This Invention and the Control Group Receiving Chemotherapy in Terms of Change in Hemoglobin Level

| | | Severity of Reaction | | | | | | | |
|---|---|---|---|---|---|---|---|---|---|
| | | 0 | | I | | II | | III | |
| Groups | Total Cases and % | Before Treatment | After Treatment | Before Treatment | After Treatment | Before Treatment | After Treatment | Before Treatment | After Treatment |
| Treatment | 30 | 22 | 26 | 6 | 4 | 2 | 0 | 0 | 0 |
| | 100% | 73.3% | 86.7% | 20% | 13.3% | 6.7% | 0% | 0% | 0% |
| Control | 30 | 23 | 17 | 6 | 10 | 1 | 3 | 0 | 0 |
| | 100% | 76.7% | 56.7% | 20% | 33.3% | 3.3% | 10% | 0% | 0% |

TABLE 39

Comparison of Toxic Reactions between the Treatment Group Receiving the Pharmaceutical Composition of *Fagopyrum cymosum* (Trev.) Meisn of This Invention and the Control Group Receiving Chemotherapy in Term of Change in Leukocyte Level

| | | Severity of Reaction | | | | | | | |
|---|---|---|---|---|---|---|---|---|---|
| | | 0 | | I | | II | | III | |
| Groups | Total Cases and % | Before Treatment | After Treatment | Before Treatment | After Treatment | Before Treatment | After Treatment | Before Treatment | After Treatment |
| Treatment | 30 | 25 | 28 | 4 | 1 | 1 | 1 | 0 | 0 |
| | 100% | 83.4% | 93.4% | 13.3% | 3.3% | 3.3% | 3.3% | 0% | 0% |
| Control | 30 | 30 | 20 | 0 | 5 | 0 | 4 | 0 | 1 |
| | 100% | 100% | 66.7% | 0% | 16.7% | 0% | 13.3% | 0% | 3.3% |

TABLE 40

Comparison of Toxic Reactions between the Treatment Group Receiving the Pharmaceutical Composition of *Fagopyrum cymosum* (Trev.) Meisn of This Invention and the Control Group Receiving Chemotherapy in Terms of Change in Platelet Level

| | | Severity of Reaction | | | | | | | |
|---|---|---|---|---|---|---|---|---|---|
| | | 0 | | I | | II | | III | |
| Groups | Total Cases and % | Before Treatment | After Treatment | Before Treatment | After Treatment | Before Treatment | After Treatment | Before Treatment | After Treatment |
| Treatment | 30 | 27 | 29 | 1 | 0 | 1 | 0 | 1 | 1 |
| | 100% | 90% | 96.7% | 3.4% | 0% | 3.3% | 0% | 3.3% | 3.3% |
| Control | 30 | 28 | 23 | 0 | 3 | 1 | 2 | 1 | 2 |
| | 100% | 93.4% | 76.6% | 0% | 10% | 3.3% | 6.7% | 3.3% | 6.7% |

Leukocyte and platelet count of patients in both treatment and control groups is shown by table 41. Leukocyte count >4000/mm$^3$ and platelet count >80000/mm$^3$ are used as the normal value. Table 41 shows that the pharmaceutical composition of *Fagopyrum cymosum* (Trev.) Meisn of this invention has no inhibiting effect on leukocyte and platelet counts.

TABLE 41

Comparison of Leukocyte and Platelet Counts of 60 Lung Cancer Patients after Treatment between the Two Groups

| Parameter | | Treatment Group (N. = 30) | Control Group (N. = 30) | $X^2$ |
|---|---|---|---|---|
| Leukocyte Count | >4000/mm$^3$ | 30 | 17 | 16.569 |
| | <4000/mm$^3$ | 0 | 13 | |

TABLE 41-continued

Comparison of Leukocyte and Platelet Counts of 60 Lung Cancer Patients after Treatment between the Two Groups

| Parameter | | Treatment Group (N. = 30) | Control Group (N. = 30) | $X^2$ |
|---|---|---|---|---|
| Platelet Count | >80000/mm$^3$ | 30 | 19 | 13.469 |
| | <80000/mm$^3$ | 0 | 11 | |

$P < 0.01$

During the clinical study, more patients in the treatment group gained weight than those in the control group. By contrast, less patients lost weight in the treatment group than those in the control group. The difference between the two groups was statistically significant (P<0.01). The definition for gaining weight in this study was that the weight of a patient increased by more than 2 kg. The definition for losing weight was that the weight of a patient decreased by more than 2 kg. The definition for stableness was that the weight of a patient increased or decreased by less than 2 kg.

TABLE 42

Effect of the Pharmaceutical Composition of *Fagopyrum cymosum* (Trev.) Meisn of This Invention on Change of Body Weight of Lung Cancer Patients

| | Treatment group | | Control Group | | |
|---|---|---|---|---|---|
| | Cases | % | Cases | % | $X^2$ |
| Increased | 6 | 20 | 2 | 6.7 | 10.2294 |
| Stable | 22 | 73.3 | 20 | 66.7 | |
| Decreased | 2 | 6.7 | 8 | 26.6 | |
| Total | 30 | 100 | 30 | 100 | |

During the clinical study, no patients in the treatment group had nausea, vomiting and diarrhea, while 9 patients in the control group had nausea and vomiting (30%) and 3 patients had diarrhea (10%) occurred in the control group. One patient in the treatment group developed slight abdominal distention after treatment with the pharmaceutical composition of *Fagopyrum cymosum* (Trev.) Meisn of this invention for one week and the symptom disappeared in two days.

During the clinical study, patients with debility increased only 6.7% in the treatment group. By contrast, patients with debility increased 33.3% in the control group. The difference between the two groups was statistically significant (P<0.01).

TABLE 45

Effect of the Pharmaceutical Composition of *Fagopyrum cymosum* (Trev.) Meisn of This Invention on Reducing the Increase of Debility of Lung Cancer Patients

| | Treatment group | | Control Group | | |
|---|---|---|---|---|---|
| | Cases | % | Cases | % | $X^2$ |
| Increased | 2 | 6.7 | 10 | 33.3 | 21.4416 |
| Stable | 28 | 93.3 | 20 | 66.7 | |
| Total | 30 | 100 | 30 | 100 | |

As for heart and kidney functions, the serum glutamic pyruvic transaminase (SGPT) level of one patient in the treatment group increased slightly during the clinical study. This patient was diagnosed later as having been infected with hepatitis C. No toxicity effects to heart or kidney functions were found in the treatment group. In contrast, the SGPT level of 3 patients in the control group increased during the clinical study while abnormal renal function with toxicity level I of blood urea nitrogen occurred in 2 patients of this group. No alopecia or injury to the nerve system was found in treatment group. The results show that the pharmaceutical composition of composition of *Fagopyrum cymosum* (Trev.) Meisn of this invention is safe for clinical application.

TABLE 43

Comparison of Gastrointestinal Reactions between the Treatment Group Receiving the Pharmaceutical Composition of *Fagopyrum cymosum* (Trev.) Meisn of This Invention and the Control Group Receiving Chemotherapy in Terms of Nausea and Vomiting Occurrence

| | | Severity of Reaction | | | | | | | |
|---|---|---|---|---|---|---|---|---|---|
| | | 0 | | I | | II | | III | |
| Groups | Total Cases and % | Before Treatment | After Treatment | Before Treatment | After Treatment | Before Treatment | After Treatment | Before Treatment | After Treatment |
| Treatment | 30 | 30 | 30 | 0 | 0 | 0 | 0 | 0 | 0 |
| | 100% | 100% | 100% | 0% | 0% | 0% | 0% | 0% | 0% |
| Control | 30 | 21 | 21 | 7 | 3 | 2 | 5 | 0 | 1 |
| | 100% | 70% | 70% | 23.33% | 10% | 6.67% | 16.67% | 0% | 3.33% |

TABLE 44

Comparison of Gastrointestinal Reactions between the Treatment Group Receiving the Pharmaceutical Composition of *Fagopyrum cymosum* (Trev.) Meisn of This Invention and the Control Group Receiving Chemotherapy in Terms of Diarrhea Occurrence

| | | Severity of Reaction | | | | | | | |
|---|---|---|---|---|---|---|---|---|---|
| | | 0 | | I | | II | | III | |
| Groups | Total Cases and % | Before Treatment | After Treatment | Before Treatment | After Treatment | Before Treatment | After Treatment | Before Treatment | After Treatment |
| Treatment | 30 | 28 | 30 | 1 | 0 | 1 | 0 | 0 | 0 |
| | 100% | 93.34% | 100% | 3.33% | 0% | 3.33% | 0% | 0% | 0% |
| Control | 30 | 27 | 27 | 1 | 2 | 2 | 1 | 0 | 0 |
| | 100% | 90% | 90% | 3.33% | 6.67% | 6.67% | 3.33% | 0% | 0% |

3. The pharmaceutical composition of *Fagopyrum cymosum* (Trev.) Meisn of this invention is effective in improving Karnofsky performance scores of lung cancer patients. Table 46 shows that Karnofsky performance scores in the treatment group rose significantly while that in the control group dropped significantly.

TABLE 46

Effects of the Pharmaceutical Composition of *Fagopyrum cymosum* (Trev.) Meisn of This Invention on Improving Karnofsky Performance Scores of Lung Cancer Patients

| Groups | Scores (Mean Value) | | Change after Treatment (Cases) | |
|---|---|---|---|---|
|  | Before Treatment | After Treatment | Score Increased | Score Decreased |
| Treatment | 60.58 | 69.44 | 20 | 4 |
| Control | 67.60 | 30.00 | 4 | 12 |

The Third Series of Clinical Study: Comparison between Therapeutic Effect of the Pharmaceutical Composition of *Fagopyrum cymosum* (Trev.) Meisn of this Invention Combined with Chemotherapy and the Effect of Chemotherapy Alone Patient Selection 80 patients with lung cancer were enrolled in the clinical study. There were 68 male patients and 12 female patients. Their age distribution is as follows:

TABLE 47

Age Distribution of 80 Lung Cancer Patients

|  | Total | 41–50 | 51–60 | 61–70 | >70 |
|---|---|---|---|---|---|
| number | 80 | 22 | 35 | 18 | 5 |
| % | 100 | 27.5 | 43.75 | 22.5 | 6.25 |

All patients were hospitalized between December, 1990 and June 1992, definitely diagnosed as having small cell lung carcinoma by anteroposterior and lateral chest tomography and CT and cytological examination (sputum or fiberoptic bronchoscopy). Clinical stages of the patients are shown in Table 48.

TABLE 48

Clinical Stages of 80 Lung Cancer Patients

|  | Total | I | II | III | IV | III ± IV |
|---|---|---|---|---|---|---|
| Cases | 80 | 3 | 19 | 35 | 23 | 58 |
| % | 100 | 3.75 | 23.75 | 43.75 | 28.75 | 72.5 |

Table 48 shows that patients at stages III and IV accounted for 72.5% of the total.

Design of the Clinical Study

Eighty patients were randomly divided into 3 groups: Group A including 20 patients, was treated by the pharmaceutical composition of *Fagopyrum cymosum* (Trev.) Meisn of this invention alone; Group B including 30 patients was treated by the pharmaceutical composition of *Fagopyrum cymosum* (Trev.) Meisn of this invention combined with chemotherapy as the experiment group; Group C including 30 patients was treated with chemotherapeutic agents alone as the control group.

Experimental Results

1. Therapeutic Effects

Effectiveness of the three different regimens was evaluated according to the established criteria of four grades: Complete Remission (CR), Partial Remission (PR), Stableness (S) and Progression (P). Comparison of therapeutic effect of the three groups is shown in table 49.

TABLE 49

Comparison of Therapeutic Effects among Three Groups

| Group | Cases | CR | PR | S | P |
|---|---|---|---|---|---|
| A | 20 (100%) | 0 (0%) | 3 (15%) | 12 (60%) | 5 (25%) |
| B | 30 (100%) | 0 (0%) | 11 (36.67%) | 14 (46.66) | 5 (16.67%) |
| C | 30 (100%) | 0 (0%) | 5 (16.67%) | 12 (40%) | 13 (43.33%) |

Table 49 indicates that the partial remission rate in Group A treated by the pharmaceutical composition of *Fagopyrum cymosum* (Trev.) Meisn of this invention alone (3/20 or 15%) was lower than that in the control group (5/30 or 16.67%). There was no statistically significant difference ($\chi^2=1.75$, $P>0.05$).

The partial remission rate and stable rate in Group B (the experiment group, 11/30 or 36.67% and 14/30 or 46.66% respectively) were higher than those in Group C (the control group, 5/30 or 16.67% and 12/30 or 40% respectively). The difference was statistically significant ($\chi^2=5.79$, $P<0.05$).

The effective rate for Group A was lower than that for Group C with no statistically significant difference ($t=1.56$, $p>0.05$). The effective rate for Group B was higher than that for Group C with statistically significant difference ($t=1.75$, $p<0.05$) and also higher than that for Group A with statistically significant difference ($t=1.67$, $p<0.05$).

The results of this experiment show that therapeutic effect of the pharmaceutical composition of *Fagopyrum cymosum* (Trev.) Meisn of this invention combined with chemotherapeutic agents is greater than that of *Fagopyrum cymosum* (Trev.) Meisn composition alone or chemotherapy alone, suggesting that the pharmaceutical composition of *Fagopyrum cymosum* (Trev.) Meisn of this invention has a synergistic effect with chemotherapy.

2. Toxic and Untoward Side Effects

TABLE 50

Comparison of Toxic and Untoward Effects in Three Groups

| Parameters | Group A (20 Cases) | | Group B (30 Cases) | | Group C (30 Cases) | |
|---|---|---|---|---|---|---|
|  | Cases | % | Cases | % | Cases | % |
| Bone Marrow Depression | 1 | 5 | 2 | 6.67 | 15 | 50 |
| Anorexia or Diminution of Food Intake | 0 | 0 | 1 | 3.33 | 26 | 86.67 |
| Nausea and Vomiting | 0 | 0 | 0 | 0 | 9 | 30 |
| Decrease in Immunity | 1 | 5 | 3 | 10 | 8 | 26.67 |
| Lowering in Functional Status | 5 | 25 | 5 | 16.67 | 17 | 56.67 |

Table 50 indicates that only 2 patients (2/30) in Group B (the experiment group) showed reduction in leucocyte and platelet counts, accounting for only 6.67% of the cases in that group, while 15 patients (15/30) in Group C (the control group) had the same manifestation, accounting for 50% of the cases in that group; the difference was statistically significant (t=3.37, p<0.01). Patients with anorexia and diminution of food intake in Group B were also much less than those in the control group (1/30 or 3.33% v. 26/30 or 86.67%). No case with nausea or vomiting appeared in Group B, while 9 cases developed these symptoms in Group C (0/30 or 0% v. 9/30 or 30%); the difference was also statistically significant (t=6.48, p=0.01). Cases of decrease of immunity in group B were less than those in Group C as well. In addition, cases with lowering in functional status in Group B (5/30 or 16.67%) were also less than those in the Group C (17/30 or 56.67%). The difference was statistically significant (t=2.78, p=0.01). From these experimental results, it is concluded that the pharmaceutical composition of *Fagopyrum cymosum* (Trev.) Meisn of this invention combined with chemotherapy can effectively reduce toxic and untoward effects of single chemotherapy.

The Fourth Series of Clinical Study: Short Term Therapeutic Effect of the Pharmaceutical Composition of *Fagopyrum cymosum* (Trev.) Meisn of this Invention Combined with Radiotherapy Patient Selection Seventy patients with lung cancer were recruited in the clinical study. They were randomly divided into 2 groups: 40 patients in the treatment group were treated by the pharmaceutical composition of *Fagopyrum cymosum* (Trev.) Meisn of this invention combined with radiotherapy. 30 patients in the control group were treated by radiotherapy alone. The age and sex distribution of the patients are as follows:

TABLE 51

Age and Sex Distribution of 70 Lung Cancer Patients

| Group | Cases | Male | Age | Mean Value of Age | Female | Age | Mean Value of Age |
|---|---|---|---|---|---|---|---|
| Treatment | 40 | 35 | 28–77 | 58.2 | 5 | 57–68 | 60.2 |
| Control | 30 | 25 | 32–68 | 56.4 | 5 | 52–67 | 60.4 |

The major clinical symptoms of the 70 lung cancer patients are as follows:

TABLE 52

Major Clinical Symptoms of 70 Lung Cancer Patients

| Groups | Total | Cough | Expectoration | Chest Pain | Bloody Sputum | Fever |
|---|---|---|---|---|---|---|
| Treatment Group | | | | | | |
| Cases | 40 | 37 | 25 | 19 | 18 | 12 |
| % | 100 | 92.5 | 62.5 | 47.5 | 45 | 30 |
| Control Group | | | | | | |
| Cases | 30 | 30 | 27 | 12 | 15 | 7 |
| % | 100 | 100 | 90 | 40 | 50 | 23.3 |

The 70 patients were staged based on "The Guiding Principles for Clinical Research of New Drugs (Traditional Chinese Materia Medica)" established by the Ministry of Health of P. R. China in 1988. Table 53 shows that the majority of the 70 patients fell into the intermediate and late stages of lung cancer.

TABLE 53

Clinical Stages of 70 Lung Cancer Patients

| Groups | Total | I | II | III | IV | III ± IV |
|---|---|---|---|---|---|---|
| Treatment | | | | | | |
| Cases | 40 | 1 | 7 | 24 | 8 | 32 |
| % | 100% | 2.5% | 17.5% | 60% | 20% | 80% |
| Control | | | | | | |
| Cases | 30 | 0 | 8 | 14 | 8 | 22 |
| % | 100% | 0% | 26.7% | 46.6% | 26.7% | 73.3% |

The pathological classifications of the 70 lung cancer patients are as follows:

TABLE 54

Pathological Classifications of 70 Lung Cancer Patients

| Groups | | Total | Squamous Carcinoma | Adenocarcinoma | Small Cell Undifferentiated Carcinoma |
|---|---|---|---|---|---|
| Treatment Group | Cases | 40 | 25 | 8 | 7 |
| | % | 100 | 62.5 | 20 | 17.5 |
| Control Group | Cases | 30 | 17 | 9 | 4 |
| | % | 100 | 56.7 | 30 | 13.3 |

All 70 patients were definitely diagnosed as having lung cancer by biopsy or brushing in fiberoptic bronchoscopy, operative exploration and cytological examination of sputum to find cancer cells in the tissues.

Methods of Treatment

Patients in both groups underwent radiotherapy with 150–200 cGy $^{60}$Co or 6–8MV electron accelerator, five times a week, in a total dose of 4000 cGy over total mediastinum and 6000 cGy for primary tumors. The dosage varied with a patient's state of sickness and tolerance.

Patients in the treatment group was further administered the pharmaceutical composition of *Fagopyrum cymosum* (Trev.) Meisn of this invention, 1.2–1.6 g. each time, 3 times a day for a course of about two months. The average duration of treatment for patients in the treatment group was 41 days and the longest 68 days. The average duration of treatment for patients in the control group was 59 days and the longest 80 days. Patients in the control group did not take the pharmaceutical composition of *Fagopyrum cymosum* (Trev.) Meisn of this invention, but received symptomatic supportive treatment.

Experimental Results

1. Therapeutic Effects

Therapeutic effectiveness was evaluated according to the established criteria of four grades: Complete Remission (CR), Partial Remission (PR), Stableness (S) and Progression (P). Comparison of therapeutic effect between the treatment and control groups is shown in Table 55.

TABLE 55

Comparison of Therapeutic Effects between the Treatment and Control Groups

| Group | Total Cases Case | % | CR Case | % | PR Case | % | S Case | % | P Case | % | Effective Rate Case | % |
|---|---|---|---|---|---|---|---|---|---|---|---|---|
| Treatment | 40 | 100 | 13 | 32.5 | 18 | 45 | 8 | 20 | 1 | 2.5 | 31 | 77.5 |
| Control | 30 | 100 | 1 | 3.3 | 14 | 46.7 | 12 | 40 | 3 | 10 | 15 | 50 |
| $X^2$ | | | 11.03 | | 0.02 | | 2.45 | | 0.67 | | 5.75 | |
| P | | | <0.01 | | >0.05 | | >0.05 | | >0.05 | | >0.05 | |

Table 55 indicates that the complete remission rate in treatment group (13/40 or 32.5%) was much higher than that in the control group (1/30 or 3.3%). The effective rate (CR+PR) in the treatment group (31/40 or 77.5%) was also much higher than that in the control group (15/30 or 50%).

At the completion of treatment, major clinical symptoms of the lung cancer patients in both groups were alleviated to some extent. By comparison, improvements in the treatment group were much more prominent. The results are shown in table 56.

TABLE 56

Alleviation of Clinical Symptoms of 70 Lung Cancer Patients in the Treatment and Control Groups

| Symptoms | Treatment N. = 40 Before Treatment Case | % | After Treatment Case | % | Control Group N. = 30 Before Treatment Case | % | After Treatment Case | % | $X^2$ | P |
|---|---|---|---|---|---|---|---|---|---|---|
| Cough | 37 | 92.5 | 13 | 32.5 | 30 | 100 | 27 | 90 | 18.4 | <0.01 |
| Expectoration | 35 | 87.5 | 21 | 52.5 | 27 | 90 | 25 | 83.3 | 6.83 | <0.01 |
| Chest Pain | 19 | 47.5 | 8 | 20 | 12 | 40 | 10 | 33.3 | 4 | <0.05 |
| Bloody Sputum | 19 | 47.5 | 3 | 7.5 | 14 | 46.7 | 6 | 20 | 4.5 | <0.05 |
| Fever | 12 | 30 | 3 | 7.5 | 7 | 23.3 | 6 | 20 | 4.65 | <0.05 |

At the completion of treatment, reduction of hemoglobin, leukocyte and platelet values to a varying extent was noted in patients in both treatment and control groups. Leukocyte count of 5 patients in the control group decreased to less than $40 \times 10^9$/L. No patient in the treatment group had leukocyte level decreased to such an extent. The results are shown in Table 57.

TABLE 57

Change in Hemoglobin, Leukocyte and Platelet Values of Lung Cancer Patients in Both Groups

| Parameters | Treatment Group N. = 40 Before Treatment | After Treatment | Control Group N. = 30 Before Treatment | After Treatment | $X^2$ | P |
|---|---|---|---|---|---|---|
| Hemoglobin (g/L) | 120.5 | 121.9 | 126.8 | 117.9 | 1.01 | >0.05 |
| Leukocytes ($\times 10^9$/L) | 8.3 | 6.5 | 7.8 | 5.6 | 2.587 | <0.05 |

TABLE 57-continued

Change in Hemoglobin, Leukocyte and Platelet Values of Lung Cancer Patients in Both Groups

| Parameters | Treatment Group N. = 40 Before Treatment | After Treatment | Control Group N. = 30 Before Treatment | After Treatment | $X^2$ | P |
|---|---|---|---|---|---|---|
| Platelet ($\times 10^9$/L) | 149.7 | 140.6 | 155.4 | 144.1 | 0.27 | >0.05 |

At the completion of treatment, a majority of patients in treatment group gained weight and better appetite, and improved their life quality. However, only a few patients in the control group exhibited these improvements. The results are shown in Table 58.

TABLE 58

Increase in Body weight and Food Intake, and Improvement in Life Quality of Lung Cancer Patients in Both Groups

| Clinical Signs | Treatment Group N. = 40 Case | % | Control Group N. = 30 Case | % | $X^2$ | P |
|---|---|---|---|---|---|---|
| Gain in weight | 18/35 | 51.42 | 4/30 | 13.33 | 7.66 | <0.01 |
| Increase of Food Intake | 21/32 | 65.62 | 1/30 | 3.33 | 23.59 | <0.01 |
| Improvement in Life Quality | 23/37 | 62.16 | 9/30 | 30 | 5.62 | <0.05 |

At the completion of treatment, all immunological parameters of patients in the treatment group increased more than those of patients in the control group, except for IgA. The differences were statistically significant as shown in Table 59.

TABLE 59

Increase of Immunological Parameters of Lung Cancer Patients in Both Groups

| Parameters | Treatment Group N. = 40 | | Control Group N. = 30 | | $X^2$ | P |
|---|---|---|---|---|---|---|
| | Case | % | Case | % | | |
| Complement C3 | 23/31 | 74.19 | 8/30 | 26.67 | 11.91 | <0.01 |
| E Rosette | 22/33 | 66.67 | 11/30 | 36.67 | 4.51 | <0.05 |
| Lymphocyte Transforming Factor | 11/13 | 84.62 | 1/10 | 10.00 | 7.54 | <0.01 |
| IgG | 20/32 | 62.50 | 7/30 | 23.33 | 8.13 | <0.01 |
| IgA | 14/32 | 43.75 | 8/30 | 26.67 | 1.30 | <0.05 |
| IgM | 22/32 | 68.75 | 12/30 | 40.00 | 4.07 | <0.05 |
| Macrophage Phagocytic Rate (%) | 26/30 | 86.67 | 11/28 | 39.29 | 12.09 | <0.01 |
| Macrophage Phagocytic Index | 18/29 | 62.07 | 9/28 | 32.14 | 4.83 | <0.05 |

At the completion of treatment, the value of liver function, kidney function and carcinoembryonic antigen (CEG) in patients were also compared between the treatment group and the control group. The results showed no statistically significant difference(P>0.05).

The results of the experiment show that application of radiotherapy combined with the pharmaceutical composition of *Fagopyrum cymosum* (Trev.) Meisn of this invention has a superior effect than application of radiotherapy alone. They also suggest that the pharmaceutical composition of *Fagopyrum cymosum* (Trev.) Meisn of this invention has a synergistic effect with radiotherapy and can alleviate the toxic and adverse effects of radiotherapy.

Reference
1. Not long ago, only two cultivated and seven wild species of buckwheat were believed to exist. However, recent seed collection and classification have resulted in a total of 14 species of buckwheat, with new discoveries continually being made every year. See Onishi, O. Discovery of New Fagopyrum Species and Its Implication for the Studies of Evolution of Fagopyrum and of the Origin of Cultivated Buckwheat. Vol. I Proc. 6th Int. Symp. Buckwheat, Aug. 26–29, 1995, Shinshu Univ., Nagano, Japan, 1995.
2. Onishi, O. Discovery of New Fagopyrum Species and Its Implication for the Studies of Evolution of Fagopyrum and of the Origin of Cultivated Buckwheat. Vol. I Proc. 6th Int. Symp. Buckwheat, Aug. 26–29, 1995, Shinshu Univ., Nagano, Japan, 1995.
3. Lou, Chunjing et al. Clinical Application and Therapeutic Effect of Composite Tartary Buckwheat Flour on Hyperglycemia and Hyperlipidaemia. Food Science, 1990, 7:45–46 (in Chinese); Wei, Yimin et al. Studies on the Physical-chemical Properties of Buckwheat Flour. J. of Cereals and Seed Oils, 1993, 3; Jiang, H. et al. Oats and Buckwheat Intakes and Cardiovascular Disease Risk Factors in an Ethnic Minority in China. Am. J. Clin. Nutr. 61:366–372, 1995.
4. Samel, D et al. The Effect of Purified Extract of *Fagopyrum esculentum* (buckwheat) on Protein Kinases Involved in Signal Transduction Pathways. Planta Med, 62(2):106–10 April 1996.
5. Antisepsis and Anti-infection Effect of Active Constituents Extracted from *Fagopyrum cymosum* (Trev.) Meisn. Yunnan Raise and Veterinarian, 2 1996; Encyclopedia of Chinese Materia Medica, Vol. 1, p. 338, Shanghai People's Publishing House, Shanghai, China, 1977.
6. Liu, W F et al. Some Pharmacological Properties of Jin Qiao Mai [*Fagopyrum cymosum* (Trev.) Meisn. (author's transl)]. Acta Pharmaceutica Sinica, 16(4): 247–52, Apr. 1981.
7. Liu, Yong Long et al. Studies on the Chemical Constituents of *Fagopyrum cymosum* (Trev.) Meisn. Acta Pharmaceutica Sinica, 18(7):545–7, July. 1983.
8. Liu TC. Growth and Accumulation of Active Constituents during Different Development Stages of *Fagopyrum cymosum* rhizome. Chung Yao Tung Pao, 8(6):5 November. 1983.
9. Yao, Rongcheng et al. Antitumor Active Constituents of Cymose Buckwheat. Acta Botanica Yunnanica, 11(2): 215–8, 1989.
10. Ma, Yunpeng et al. Prediction of Responsiveness of Human Lung Cancer Xenograft to Extracts of *Fagopyrum cymosum* (Trev.) Meisn by SRC Assay. Chinese Tumor Clinic, 16(5):309–12, 1989.
11. Liang, Xiaozhong et al. TLC Scanning Determination of Procyanidin B-2 in *Fagopyrum Dibotrys* Rhizome. Chinese Journal of Pharmaceutical Analysis, 10(4): 227–30, 1990.
12. Liang Mingda et al. Extracorporeal Anticancer Function of *Fagopyrum cymosum* Rootin. Yunnan Medicine, 12(6):364–9, 1991.
13. Ma Mingfu et al. Mutagenicity and Teratogenicitic Tests of *Fagopyrum Cymosum* (Trev.) Meisn. Hereditas, 13(3):24–6, 1991.
14. Gao Z. et al. Effect of *Fagopyrum cymosum* Rootin on Clonal Formation of Four Human Tumor Cells. Journal of Chinese Materia Medica, 18(8):498–500, 511 August 1993.
15. Zhang Wenjie et al. Phenolic Constituents from *Fagopyrum Dibotrys*. Acta Botanica Yunnanica, 16(4): 354–6, 1994.
16. Meng Fanhong et al. Anticancer Effect of Cymose Buckwheat Roots on Human Tumor Cells Cultured in Vitro. Academic Journal of Kunming Medical College, 15(2):18–22, 1994.
17. Meng Fanhong et al. Studies on Anticancer Effect of Jin E in vitro. Cancer, 13(3):265–6, 1994.
18. Peng Yong et al. Research and Development of *Fagopyrum Dibotrys*. Chinese Herb, 27(10):629–31, 1996.

What is claimed is:

1. A method for treating lung cancer or alleviating clinical symptoms of lung cancer in a subject comprising administering to the subject an effective amount of the composition comprising:
   a) 30–70% tannin content; and
   b) 0.2–1.0% (-)epicatechin.

2. The method of claim 1, wherein the symptom of expectoration of the subject is alleviated.

3. The method of claim 1, wherein the symptom of chest pain of the subject is alleviated.

4. The method of claim 1, wherein the symptom of bloody sputum of the subject is alleviated.

5. The method of claim 1, wherein the symptom of fever of the subject is alleviated.

6. The method of claim 1, wherein the quality of blood of the subject is improved.

7. The method of claim 1, wherein the hemoglobin, leucocyte, or platelet count of the subject increases.

8. The method of claim 1, wherein the daily food consumption or body weight of the subject increases.

9. The method of claim 1, wherein the nausea or vomiting occurrence of the subject decreases.

10. The method of claim 1 wherein diarrhea occurrence of the subject decreases.

11. The method of claim 1 wherein debility occurrence of the subject decreases.

12. The method of claim 1 wherein the blood sedimentation rate of the subject decreases.

13. The method of claim 1 wherein the blood urea nitrogen of the subject decreases.

14. The method of claim 1 wherein the Karnofsky performance scores of the subject improved.

15. The method of claim 1 further comprising chemotherapy or radiotherapy.

16. The method of claim 15 wherein complement C3 level of the subject increases.

17. The method of claim 15 where E Rosette level of the subject increases.

18. The method of claim 15 wherein the lymphocyte transforming factor, IgA, IgG, or IgM of the subject increases.

19. A method for improving clinical signs in a subject suffering from lung cancer comprising administering to the subject an effective amount of the composition comprising:
a) 30–70% tannin content; and
b) 0.2–1% (–) epicatechin.

20. A method for alleviating the symptom of cough in a subject suffering from common cold, bronchitis, pneumonia, pulmonary tuberculosis, pulmonary abscess, lung cancer, and upper respiratory track infection comprising administering to the subject an effective amount of the composition comprising:
a) 30–70% tannin content; and
b) 0.2–1.0% (–) epicatechin.

* * * * *